United States Patent
Brunsvold et al.

(10) Patent No.: US 12,419,630 B2
(45) Date of Patent: **\*Sep. 23, 2025**

(54) SURGICAL TOOL AND METHOD OF USE

(71) Applicant: PARCUS MEDICAL, LLC, Sarasota, FL (US)

(72) Inventors: Mark D. Brunsvold, Sarasota, FL (US); Bart Bracy, Orlando, FL (US)

(73) Assignee: PARCUS MEDICAL, LLC, Sarasota, FL (US)

( \* ) Notice: Subject to any disclaimer, the term of this patent is extended or adjusted under 35 U.S.C. 154(b) by 182 days.

This patent is subject to a terminal disclaimer.

(21) Appl. No.: 17/981,046

(22) Filed: Nov. 4, 2022

(65) Prior Publication Data

US 2023/0054565 A1 Feb. 23, 2023
US 2023/0380828 A9 Nov. 30, 2023

Related U.S. Application Data

(63) Continuation of application No. 16/551,705, filed on Aug. 26, 2019, now Pat. No. 11,517,301, which is a continuation-in-part of application No. 16/206,736, filed on Nov. 30, 2018, now Pat. No. 11,457,912, which is a continuation of application No. PCT/US2017/035792, filed on Jun. 2, 2017.

(60) Provisional application No. 62/724,599, filed on Aug. 29, 2018, provisional application No. 62/722,976, filed on Aug. 26, 2018, provisional application No. 62/368,023, filed on Jul. 28, 2016, provisional application No. 62/344,489, filed on Jun. 2, 2016.

(51) Int. Cl.
A61B 17/04 (2006.01)

(52) U.S. Cl.
CPC .. *A61B 17/0401* (2013.01); *A61B 2017/0409* (2013.01); *A61B 2017/0414* (2013.01); *A61B 2017/0445* (2013.01); *A61B 2017/0496* (2013.01)

(58) Field of Classification Search
CPC . A61B 17/04; A61B 17/0401; A61B 17/0483; A61B 17/06004; A61B 2017/0409; A61B 2017/0496; A61B 2017/0445; A61B 2017/0414

See application file for complete search history.

(56) References Cited

U.S. PATENT DOCUMENTS 5,207,679 A 5/1993 Li
5,948,000 A 9/1999 Larsen et al.
(Continued)

OTHER PUBLICATIONS

International Search Report and Written Opinion for International Patent Application No. PCT/US2017/035792 mailed on Sep. 1, 2017, 6 pages.
(Continued)

*Primary Examiner* — Vi X Nguyen
(74) *Attorney, Agent, or Firm* — GOODWIN PROCTER LLP

(57) ABSTRACT

A surgical tool incorporates a suture guide with an anchor driver supporting an anchor where the anchor is maintained at a distance from the suture guide until release of a detent mechanism. Thereafter, the anchor is allowed to move into proximity to the suture guide, fixing a suture supported by the suture guide to a substrate, the entire procedure being achievable with a single hand.

10 Claims, 26 Drawing Sheets

(56) References Cited

U.S. PATENT DOCUMENTS

| | | | |
|---|---|---|---|
| 6,036,694 A * | 3/2000 | Goble | A61F 2/0811 |
| | | | 623/13.13 |
| 6,083,522 A * | 7/2000 | Chu | B29C 48/70 |
| | | | 623/22.11 |
| 11,517,301 B2 * | 12/2022 | Brunsvold | A61B 17/0401 |
| 2002/0062127 A1 | 5/2002 | Schumacher et al. | |
| 2002/0115999 A1 | 8/2002 | McDevitt et al. | |
| 2002/0128654 A1 | 9/2002 | Steger et al. | |
| 2003/0028253 A1 | 2/2003 | Stone et al. | |
| 2003/0125743 A1 | 7/2003 | Roman et al. | |
| 2003/0208276 A1 | 11/2003 | Berelsman et al. | |
| 2004/0127908 A1 | 7/2004 | Roman et al. | |
| 2004/0153161 A1 | 8/2004 | Stone et al. | |
| 2004/0254646 A1 | 12/2004 | Stone et al. | |
| 2004/0260298 A1 | 12/2004 | Kaiser et al. | |
| 2005/0004675 A1 | 1/2005 | Shultz et al. | |
| 2005/0107882 A1 | 5/2005 | Stone et al. | |
| 2005/0119696 A1 | 6/2005 | Walters et al. | |
| 2005/0197708 A1 | 9/2005 | Stone et al. | |
| 2005/0273003 A1 | 12/2005 | Walters et al. | |
| 2005/0277961 A1 | 12/2005 | Stone et al. | |
| 2006/0020344 A1 | 1/2006 | Shultz et al. | |
| 2006/0029633 A1 | 2/2006 | Kaiser et al. | |
| 2006/0036330 A1 | 2/2006 | Shultz et al. | |
| 2006/0100627 A1 | 5/2006 | Stone et al. | |
| 2006/0111729 A1 | 5/2006 | Bacastow et al. | |
| 2006/0173546 A1 | 8/2006 | Berelsman et al. | |
| 2006/0189993 A1 | 8/2006 | Stone | |
| 2006/0190042 A1 | 8/2006 | Stone et al. | |
| 2006/0235413 A1 | 10/2006 | Denham et al. | |
| 2006/0247642 A1 | 11/2006 | Stone et al. | |
| 2006/0282085 A1 | 12/2006 | Stone et al. | |
| 2006/0293685 A1 | 12/2006 | Stone et al. | |
| 2007/0038230 A1 | 2/2007 | Stone et al. | |
| 2007/0038299 A1 | 2/2007 | Stone et al. | |
| 2007/0049944 A1 | 3/2007 | Stone et al. | |
| 2007/0141110 A1 | 6/2007 | Stone et al. | |
| 2007/0142918 A1 | 6/2007 | Stone | |
| 2007/0156174 A1 | 7/2007 | Kaiser et al. | |
| 2007/0179510 A1 | 8/2007 | Stone | |
| 2007/0179624 A1 | 8/2007 | Stone et al. | |
| 2007/0185532 A1 | 8/2007 | Stone et al. | |
| 2007/0191853 A1 | 8/2007 | Stone | |
| 2007/0208294 A1 | 9/2007 | Stone | |
| 2007/0225719 A1 | 9/2007 | Stone et al. | |
| 2007/0225735 A1 | 9/2007 | Stone et al. | |
| 2008/0015706 A1 | 1/2008 | Berelsman et al. | |
| 2008/0021554 A1 | 1/2008 | Stone et al. | |
| 2008/0027446 A1 | 1/2008 | Stone et al. | |
| 2008/0033566 A1 | 2/2008 | Berelsman et al. | |
| 2008/0065114 A1 | 3/2008 | Stone et al. | |
| 2008/0082127 A1 | 4/2008 | Stone et al. | |
| 2008/0082128 A1 | 4/2008 | Stone | |
| 2008/0086138 A1 | 4/2008 | Stone et al. | |
| 2008/0097453 A1 | 4/2008 | Stone | |
| 2008/0132932 A1 | 6/2008 | Hoeppner et al. | |
| 2008/0140092 A1 | 6/2008 | Stone et al. | |
| 2008/0140093 A1 | 6/2008 | Stone et al. | |
| 2008/0161852 A1 | 7/2008 | Kaiser et al. | |
| 2008/0215055 A1 | 9/2008 | Stone | |
| 2008/0228271 A1 | 9/2008 | Stone et al. | |
| 2008/0243248 A1 | 10/2008 | Stone et al. | |
| 2008/0249632 A1 | 10/2008 | Stone et al. | |
| 2008/0255613 A1 | 10/2008 | Kaiser et al. | |
| 2008/0269674 A1 | 10/2008 | Stone | |
| 2008/0275431 A1 | 11/2008 | Stone et al. | |
| 2008/0281325 A1 | 11/2008 | Stone et al. | |
| 2008/0306490 A1 | 12/2008 | Lakin et al. | |
| 2008/0312689 A1 | 12/2008 | Denham et al. | |
| 2009/0054928 A1 | 2/2009 | Denham et al. | |
| 2009/0062854 A1 | 3/2009 | Kaiser et al. | |
| 2009/0082805 A1 | 3/2009 | Kaiser et al. | |
| 2009/0192468 A1 | 7/2009 | Stone | |
| 2009/0204146 A1 | 8/2009 | Kaiser et al. | |
| 2009/0281555 A1 | 11/2009 | Stone | |
| 2009/0306684 A1 | 12/2009 | Stone et al. | |
| 2009/0306711 A1 | 12/2009 | Stone et al. | |
| 2009/0312776 A1 | 12/2009 | Kaiser et al. | |
| 2009/0318961 A1 | 12/2009 | Stone et al. | |
| 2010/0010636 A1 | 1/2010 | Shultz et al. | |
| 2010/0087857 A1 | 4/2010 | Stone et al. | |
| 2010/0145384 A1 | 6/2010 | Stone et al. | |
| 2010/0152782 A1 | 6/2010 | Stone et al. | |
| 2010/0179661 A1 | 7/2010 | Berelsman et al. | |
| 2010/0211075 A1 | 8/2010 | Stone | |
| 2010/0222791 A1 | 9/2010 | Stone et al. | |
| 2010/0222812 A1 | 9/2010 | Stone et al. | |
| 2010/0256642 A1 | 10/2010 | Stone | |
| 2010/0268233 A1 | 10/2010 | Stone | |
| 2010/0268275 A1 | 10/2010 | Stone et al. | |
| 2010/0286795 A1 | 11/2010 | Stone et al. | |
| 2010/0292792 A1 | 11/2010 | Stone et al. | |
| 2010/0305698 A1 | 12/2010 | Metzger et al. | |
| 2010/0305709 A1 | 12/2010 | Metzger et al. | |
| 2010/0312341 A1 | 12/2010 | Kaiser et al. | |
| 2011/0004258 A1 | 1/2011 | Stone et al. | |
| 2011/0015740 A1 | 1/2011 | Metzger et al. | |
| 2011/0035015 A1 | 2/2011 | Stone et al. | |
| 2011/0054526 A1 | 3/2011 | Stone et al. | |
| 2011/0087284 A1 | 4/2011 | Stone et al. | |
| 2011/0098727 A1 | 4/2011 | Kaiser et al. | |
| 2011/0100173 A1 | 5/2011 | Stone et al. | |
| 2011/0106153 A1 | 5/2011 | Stone et al. | |
| 2011/0153018 A1 | 6/2011 | Walters et al. | |
| 2011/0160767 A1 | 6/2011 | Stone et al. | |
| 2011/0160768 A1 | 6/2011 | Stone et al. | |
| 2011/0166578 A1 | 7/2011 | Stone et al. | |
| 2011/0208239 A1 | 8/2011 | Stone et al. | |
| 2011/0208240 A1 | 8/2011 | Stone et al. | |
| 2011/0213376 A1 | 9/2011 | Maxson et al. | |
| 2011/0218625 A1 | 9/2011 | Berelsman et al. | |
| 2011/0224799 A1 | 9/2011 | Stone | |
| 2011/0264141 A1 | 10/2011 | Denham et al. | |
| 2011/0270306 A1 | 11/2011 | Denham et al. | |
| 2011/0295279 A1 | 12/2011 | Stone et al. | |
| 2011/0301708 A1 | 12/2011 | Stone et al. | |
| 2012/0041485 A1 | 2/2012 | Kaiser et al. | |
| 2012/0041486 A1 | 2/2012 | Stone et al. | |
| 2012/0046693 A1 | 2/2012 | Denham et al. | |
| 2012/0053630 A1 | 3/2012 | Denham et al. | |
| 2012/0059417 A1 | 3/2012 | Norton et al. | |
| 2012/0059418 A1 | 3/2012 | Denham et al. | |
| 2012/0078375 A1 | 3/2012 | Smith et al. | |
| 2012/0089193 A1 | 4/2012 | Stone et al. | |
| 2012/0095470 A1 | 4/2012 | Kaiser et al. | |
| 2012/0095565 A1 | 4/2012 | Shultz et al. | |
| 2012/0109321 A1 | 5/2012 | Stone et al. | |
| 2012/0116409 A1 | 5/2012 | Stone | |
| 2012/0116452 A1 | 5/2012 | Stone et al. | |
| 2012/0150297 A1 | 6/2012 | Denham et al. | |
| 2012/0150307 A1 | 6/2012 | Metzger et al. | |
| 2012/0165866 A1 | 6/2012 | Kaiser et al. | |
| 2012/0165867 A1 | 6/2012 | Denham et al. | |
| 2012/0165938 A1 | 6/2012 | Denham et al. | |
| 2012/0172986 A1 | 7/2012 | Stone et al. | |
| 2012/0245585 A1 | 9/2012 | Kaiser et al. | |
| 2012/0245698 A1 | 9/2012 | Stone et al. | |
| 2012/0296345 A1 | 11/2012 | Wack et al. | |
| 2012/0296427 A1 | 11/2012 | Conner et al. | |
| 2012/0303046 A1 | 11/2012 | Stone et al. | |
| 2012/0310245 A1 | 12/2012 | Hoeppner et al. | |
| 2013/0012962 A1 | 1/2013 | Stone | |
| 2013/0023930 A1 | 1/2013 | Stone et al. | |
| 2013/0035698 A1 | 2/2013 | Stone et al. | |
| 2013/0046341 A1 | 2/2013 | Stone et al. | |
| 2013/0079780 A1 | 3/2013 | Wagner et al. | |
| 2013/0096678 A1 | 4/2013 | Denham | |
| 2013/0103082 A1 | 4/2013 | Kaiser et al. | |
| 2013/0110251 A1 | 5/2013 | Metzger et al. | |
| 2013/0116730 A1 | 5/2013 | Denham et al. | |
| 2013/0123813 A1 | 5/2013 | Stone et al. | |
| 2013/0138123 A1 | 5/2013 | Stone et al. | |
| 2013/0138152 A1 | 5/2013 | Stone et al. | |
| 2013/0144337 A1 | 6/2013 | Stone et al. | |

(56) References Cited

U.S. PATENT DOCUMENTS

| | | |
|---|---|---|
| 2013/0144338 A1 | 6/2013 | Stone et al. |
| 2013/0144397 A1 | 6/2013 | Smith et al. |
| 2013/0158601 A1 | 6/2013 | Stone et al. |
| 2013/0172944 A1 | 7/2013 | Fritzinger et al. |
| 2013/0184764 A1 | 7/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0245761 A1 | 9/2013 | Conner et al. |
| 2013/0304120 A1 | 11/2013 | Stone et al. |
| 2013/0317612 A1 | 11/2013 | Stone et al. |
| 2013/0317621 A1 | 11/2013 | Metzger et al. |
| 2013/0325063 A1 | 12/2013 | Norton et al. |
| 2013/0331848 A1 | 12/2013 | Kaiser et al. |
| 2013/0331885 A1 | 12/2013 | Stone et al. |
| 2014/0046367 A1 | 2/2014 | Stone et al. |
| 2014/0046368 A1 | 2/2014 | Kaiser et al. |
| 2014/0066982 A1 | 3/2014 | Stone et al. |
| 2014/0067081 A1 | 3/2014 | Stone |
| 2014/0074160 A1 | 3/2014 | Denham et al. |
| 2014/0088655 A1 | 3/2014 | Stone et al. |
| 2014/0094913 A1 | 4/2014 | Berelsman et al. |
| 2014/0107657 A1 | 4/2014 | Norton et al. |
| 2014/0107715 A1 | 4/2014 | Heilman et al. |
| 2014/0135775 A1 | 5/2014 | Maxson et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0207158 A1 | 7/2014 | Stone et al. |
| 2014/0214100 A1 | 7/2014 | Norton |
| 2014/0236191 A1 | 8/2014 | Stone et al. |
| 2014/0236309 A1 | 8/2014 | Smith et al. |
| 2014/0257378 A1 | 9/2014 | Norton et al. |
| 2014/0276819 A1 | 9/2014 | Cresina et al. |
| 2014/0276826 A1 | 9/2014 | Metzinger et al. |
| 2014/0276992 A1 | 9/2014 | Stone et al. |
| 2014/0277447 A1 | 9/2014 | Berelsman et al. |
| 2014/0296988 A1 | 10/2014 | Winslow et al. |
| 2014/0324101 A1 | 10/2014 | Denham et al. |
| 2014/0330311 A1 | 11/2014 | Denham et al. |
| 2014/0350674 A1 | 11/2014 | Stone et al. |
| 2014/0364906 A1 | 12/2014 | Palese et al. |
| 2014/0378979 A1 | 12/2014 | Stone et al. |
| 2015/0005820 A1 | 1/2015 | Finley et al. |
| 2015/0012015 A1 | 1/2015 | Berelsman et al. |
| 2015/0012016 A1 | 1/2015 | Stone |
| 2015/0012094 A1 | 1/2015 | Denham et al. |
| 2015/0018880 A1 | 1/2015 | Stone et al. |
| 2015/0025643 A1 | 1/2015 | Stone et al. |
| 2015/0057757 A1 | 2/2015 | Metzger et al. |
| 2015/0073417 A1 | 3/2015 | Norton et al. |
| 2015/0094739 A1 | 4/2015 | Norton et al. |
| 2015/0119890 A1 | 4/2015 | Kaiser et al. |
| 2015/0127051 A1 | 5/2015 | Kaiser et al. |
| 2015/0134000 A1 | 5/2015 | Denham et al. |
| 2015/0134001 A1 | 5/2015 | Stone et al. |
| 2015/0141995 A1 | 5/2015 | Norton |
| 2015/0173742 A1 | 6/2015 | Palese et al. |
| 2015/0173743 A1 | 6/2015 | Palese et al. |
| 2015/0173754 A1 | 6/2015 | Norton et al. |
| 2015/0173887 A1 | 6/2015 | Berelsman et al. |
| 2015/0257749 A1 | 9/2015 | Denham et al. |
| 2015/0257750 A1 | 9/2015 | Kaiser et al. |
| 2015/0342587 A1 | 12/2015 | Norton et al. |
| 2015/0342594 A1 | 12/2015 | Stone |
| 2015/0342595 A1 | 12/2015 | Norton |
| 2015/0354751 A1 | 12/2015 | Slagle et al. |
| 2016/0000483 A1 | 1/2016 | Stone |
| 2016/0022261 A1 | 1/2016 | Stone et al. |
| 2016/0038131 A1 | 2/2016 | White et al. |
| 2016/0058436 A1 | 3/2016 | Stone et al. |
| 2016/0081789 A1 | 3/2016 | Denham et al. |
| 2016/0089130 A1 | 3/2016 | Hoeppner et al. |
| 2016/0089138 A1 | 3/2016 | Early et al. |
| 2016/0106414 A1 | 4/2016 | Stone et al. |
| 2016/0113691 A1 | 4/2016 | Fritzinger et al. |
| 2016/0128683 A1 | 5/2016 | Denham et al. |
| 2016/0128684 A1 | 5/2016 | Stone et al. |
| 2016/0183935 A1 | 6/2016 | Stone |
| 2016/0199053 A1 | 7/2016 | Norton et al. |
| 2016/0199115 A1 | 7/2016 | Anderson et al. |
| 2016/0206307 A1 | 7/2016 | Wack et al. |
| 2016/0213369 A1 | 7/2016 | Stone et al. |
| 2016/0213480 A1 | 7/2016 | Stone et al. |
| 2016/0242760 A1 | 8/2016 | Kaiser et al. |
| 2016/0242793 A1 | 8/2016 | Norton et al. |
| 2016/0270822 A1 | 9/2016 | Cresina et al. |
| 2016/0270923 A1 | 9/2016 | Finley et al. |
| 2016/0287242 A1 | 10/2016 | Troxel et al. |
| 2016/0310128 A1 | 10/2016 | Denham |
| 2016/0310129 A1 | 10/2016 | Hoeppner et al. |
| 2016/0310186 A1 | 10/2016 | Hoeppner et al. |
| 2016/0361073 A1 | 12/2016 | Heilman et al. |
| 2017/0014225 A1 | 1/2017 | Denham et al. |
| 2017/0020507 A1 | 1/2017 | Denham et al. |
| 2017/0035411 A1 | 2/2017 | Kaiser et al. |
| 2017/0049557 A1 | 2/2017 | Denham et al. |
| 2017/0065278 A1 | 3/2017 | Stone et al. |
| 2017/0071595 A1 | 3/2017 | Stone et al. |
| 2017/0079799 A1 | 3/2017 | Smith et al. |
| 2017/0086816 A1 | 3/2017 | Norton |
| 2017/0119382 A1 | 5/2017 | Denham et al. |
| 2017/0128215 A1 | 5/2017 | Denham |
| 2017/0151054 A1 | 6/2017 | Stone et al. |
| 2017/0172561 A1 | 6/2017 | Denham |
| 2017/0172604 A1 | 6/2017 | Denham |
| 2017/0181746 A1 | 6/2017 | Denham et al. |
| 2017/0189011 A1 | 7/2017 | Stone et al. |
| 2017/0202587 A1 | 7/2017 | Stone et al. |
| 2017/0215876 A1 | 8/2017 | Norton et al. |
| 2017/0266014 A1 | 9/2017 | Stone et al. |
| 2017/0273686 A1 | 9/2017 | Denham et al. |
| 2017/0290579 A1 | 10/2017 | Norton |
| 2017/0311947 A1 | 11/2017 | Kaiser et al. |
| 2017/0319195 A1 | 11/2017 | Denham et al. |
| 2017/0319204 A1 | 11/2017 | Norton et al. |
| 2017/0325808 A1 | 11/2017 | Stone et al. |
| 2017/0333176 A1 | 11/2017 | Stone et al. |
| 2017/0354509 A1 | 12/2017 | Finley et al. |
| 2017/0360425 A1 | 12/2017 | Stone et al. |
| 2018/0000477 A1 | 1/2018 | Kaiser et al. |
| 2018/0014864 A1 | 1/2018 | Stone et al. |
| 2018/0021036 A1 | 1/2018 | Kaiser et al. |
| 2018/0021125 A1 | 1/2018 | Berelsman et al. |
| 2018/0042609 A1 | 2/2018 | Denham et al. |
| 2018/0085119 A1 | 3/2018 | Stone et al. |
| 2018/0125475 A1 | 5/2018 | Lozier et al. |
| 2018/0125476 A1 | 5/2018 | Kaiser et al. |
| 2018/0125477 A1 | 5/2018 | Stone |
| 2018/0132871 A1 | 5/2018 | Heilman et al. |
| 2018/0153538 A1 | 6/2018 | Kaiser et al. |
| 2018/0153565 A1 | 6/2018 | Stone et al. |
| 2018/0161030 A1 | 6/2018 | Stone et al. |
| 2018/0177501 A1 | 6/2018 | Kaiser et al. |
| 2018/0193015 A1 | 7/2018 | Denham et al. |
| 2018/0221017 A1 | 8/2018 | Stone et al. |
| 2018/0235595 A1 | 8/2018 | Palese et al. |
| 2018/0235597 A1 | 8/2018 | Troxel et al. |
| 2018/0235747 A1 | 8/2018 | Berelsman et al. |
| 2018/0249997 A1 | 9/2018 | Stone et al. |
| 2018/0256152 A1 | 9/2018 | Palese et al. |
| 2018/0256153 A1 | 9/2018 | Stone et al. |
| 2018/0338755 A1 | 11/2018 | Palese et al. |
| 2019/0046185 A1 | 2/2019 | Norton et al. |
| 2019/0083233 A1 | 3/2019 | Denham et al. |
| 2019/0150909 A1 | 5/2019 | Stone et al. |
| 2019/0150923 A1 | 5/2019 | Stone et al. |
| 2019/0159772 A1 | 5/2019 | Norton et al. |
| 2019/0231348 A1 | 8/2019 | Stone et al. |
| 2019/0231371 A1 | 8/2019 | Maxson et al. |
| 2019/0254652 A1 | 8/2019 | Stone et al. |

(56) References Cited

U.S. PATENT DOCUMENTS

| | | |
|---|---|---|
| 2019/0274681 A1 | 9/2019 | Denham et al. |
| 2019/0282227 A1 | 9/2019 | Norton |
| 2019/0290258 A1 | 9/2019 | Denham et al. |
| 2019/0298345 A1 | 10/2019 | Denham et al. |
| 2019/0328382 A1 | 10/2019 | Stone et al. |
| 2019/0350577 A1 | 11/2019 | Norton et al. |
| 2019/0365376 A1 | 12/2019 | Stone et al. |
| 2020/0029955 A1 | 1/2020 | Stone et al. |
| 2020/0069304 A1 | 3/2020 | Norton |
| 2020/0085562 A1 | 3/2020 | Stone et al. |
| 2020/0107937 A1 | 4/2020 | Denham et al. |
| 2020/0129214 A1 | 4/2020 | Pepper et al. |
| 2020/0178959 A1 | 6/2020 | Denham et al. |
| 2020/0187932 A1 | 6/2020 | Kaiser et al. |
| 2020/0187933 A1 | 6/2020 | Kaiser et al. |
| 2020/0188003 A1 | 6/2020 | Schlotterback et al. |
| 2020/0197002 A1 | 6/2020 | Stone et al. |
| 2020/0222042 A1 | 7/2020 | Berelsman et al. |
| 2020/0281637 A1 | 9/2020 | Denham |
| 2020/0297338 A1 | 9/2020 | Stone et al. |
| 2020/0337697 A1 | 10/2020 | Norton et al. |
| 2020/0367880 A1 | 11/2020 | Stone et al. |
| 2021/0038233 A1 | 2/2021 | Heilman et al. |
| 2021/0077131 A1 | 3/2021 | Denham et al. |
| 2021/0121171 A1 | 4/2021 | Palese et al. |
| 2021/0137514 A1 | 5/2021 | Lawhorn et al. |
| 2021/0177397 A1 | 6/2021 | Stone et al. |
| 2021/0228203 A1 | 7/2021 | Denham et al. |
| 2021/0244443 A1 | 8/2021 | Coyne et al. |
| 2021/0290250 A1 | 9/2021 | Denham et al. |
| 2021/0315555 A1 | 10/2021 | Denham et al. |
| 2021/0315656 A1 | 10/2021 | Denham et al. |
| 2021/0315657 A1 | 10/2021 | Denham et al. |
| 2021/0330311 A1 | 10/2021 | Denham et al. |
| 2021/0361286 A1 | 11/2021 | Stone et al. |
| 2021/0401477 A1 | 12/2021 | Weiner et al. |
| 2022/0054123 A1 | 2/2022 | Kaiser et al. |
| 2022/0061861 A1 | 3/2022 | Coyne et al. |
| 2022/0087672 A1 | 3/2022 | Norton |

OTHER PUBLICATIONS

File History for U.S. Appl. No. 16/206,736.
File History for U.S. Appl. No. 16/551,705.
File History for U.S. Serial No. PCT/US2017/05792.
File History for U.S. Appl. No. 62/344,489.
File History for U.S. Appl. No. 62/368,023.
File History for U.S. Appl. No. 62/722,976.
File History for U.S. Appl. No. 62/724,599.

* cited by examiner

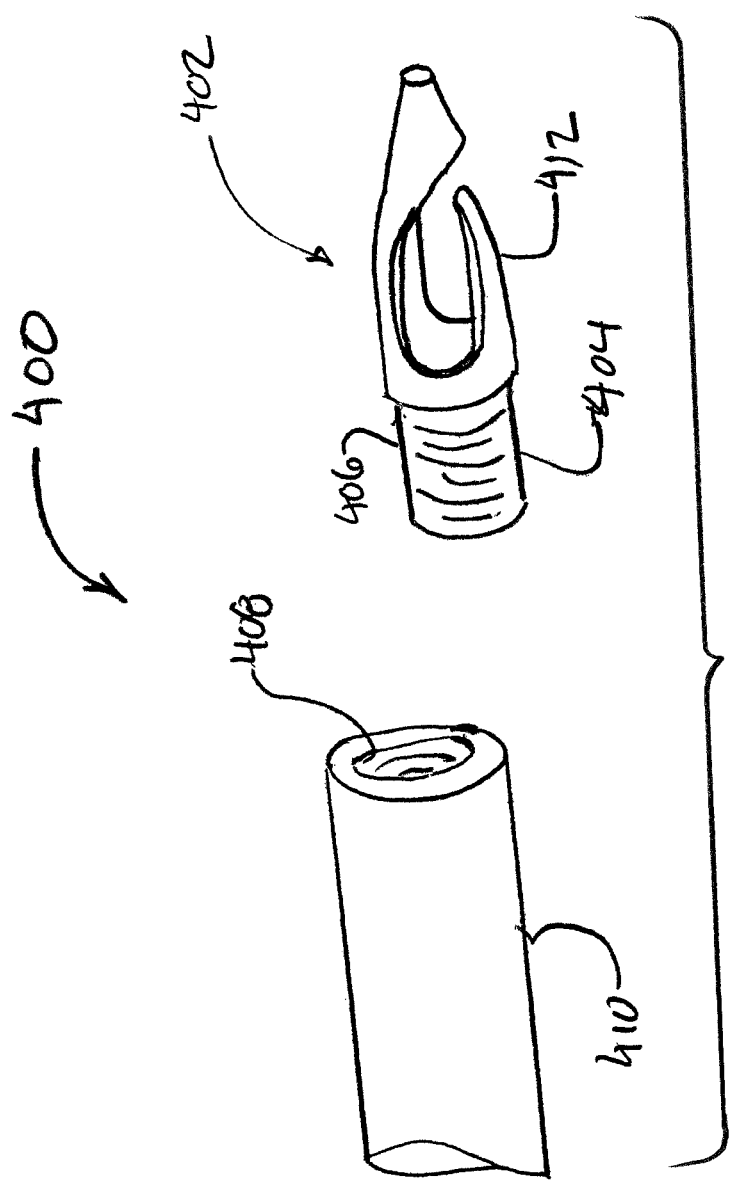

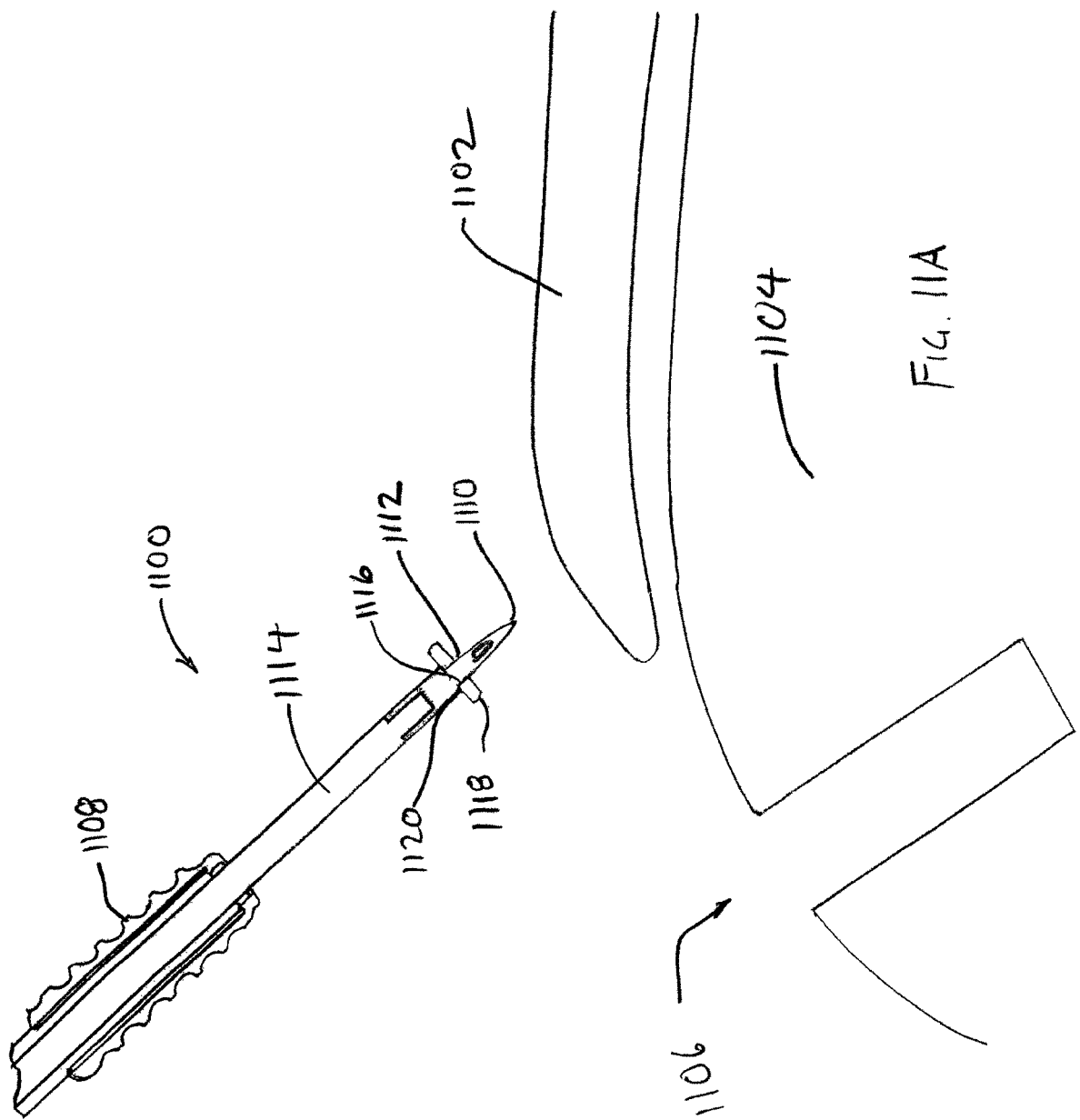

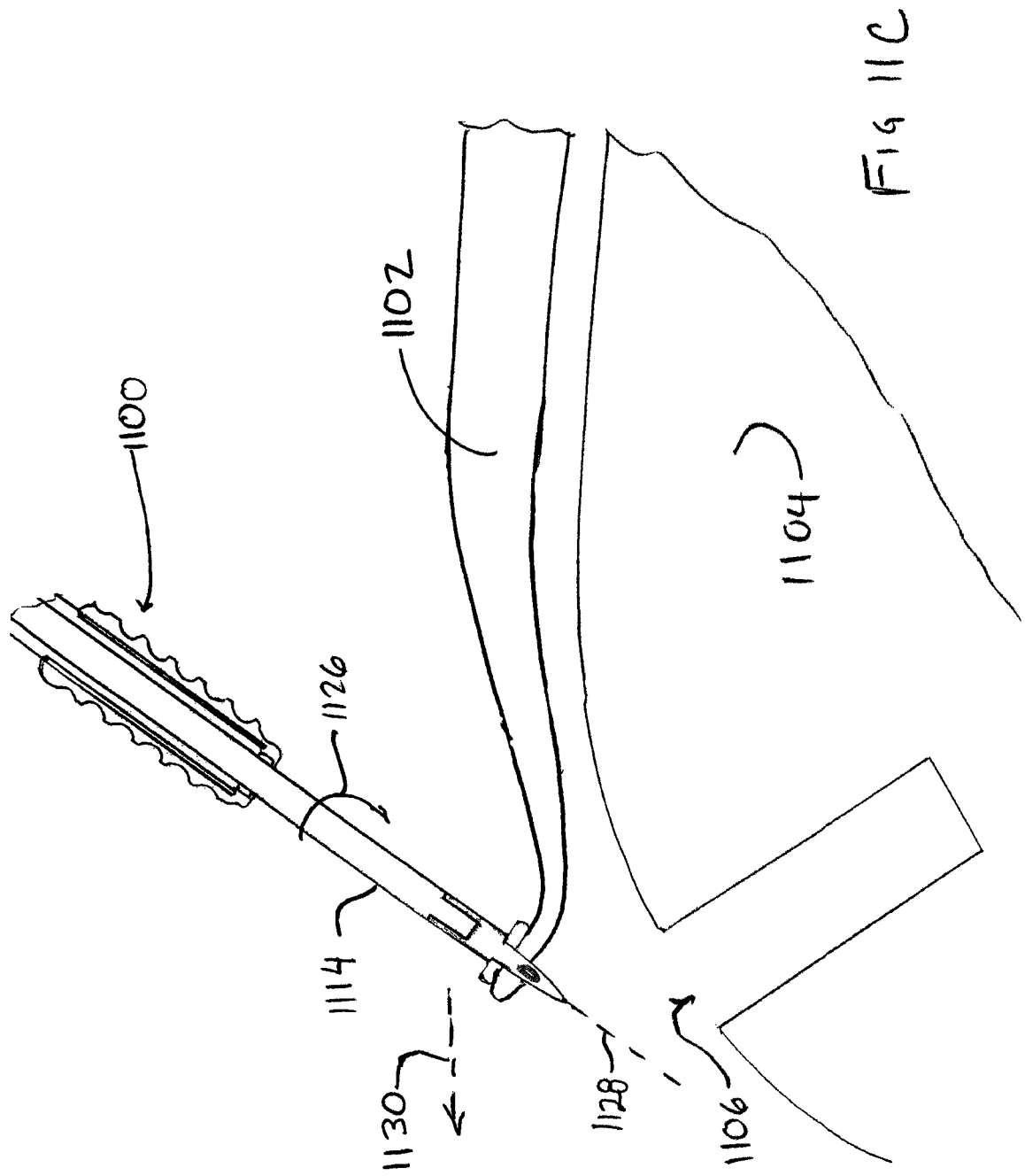

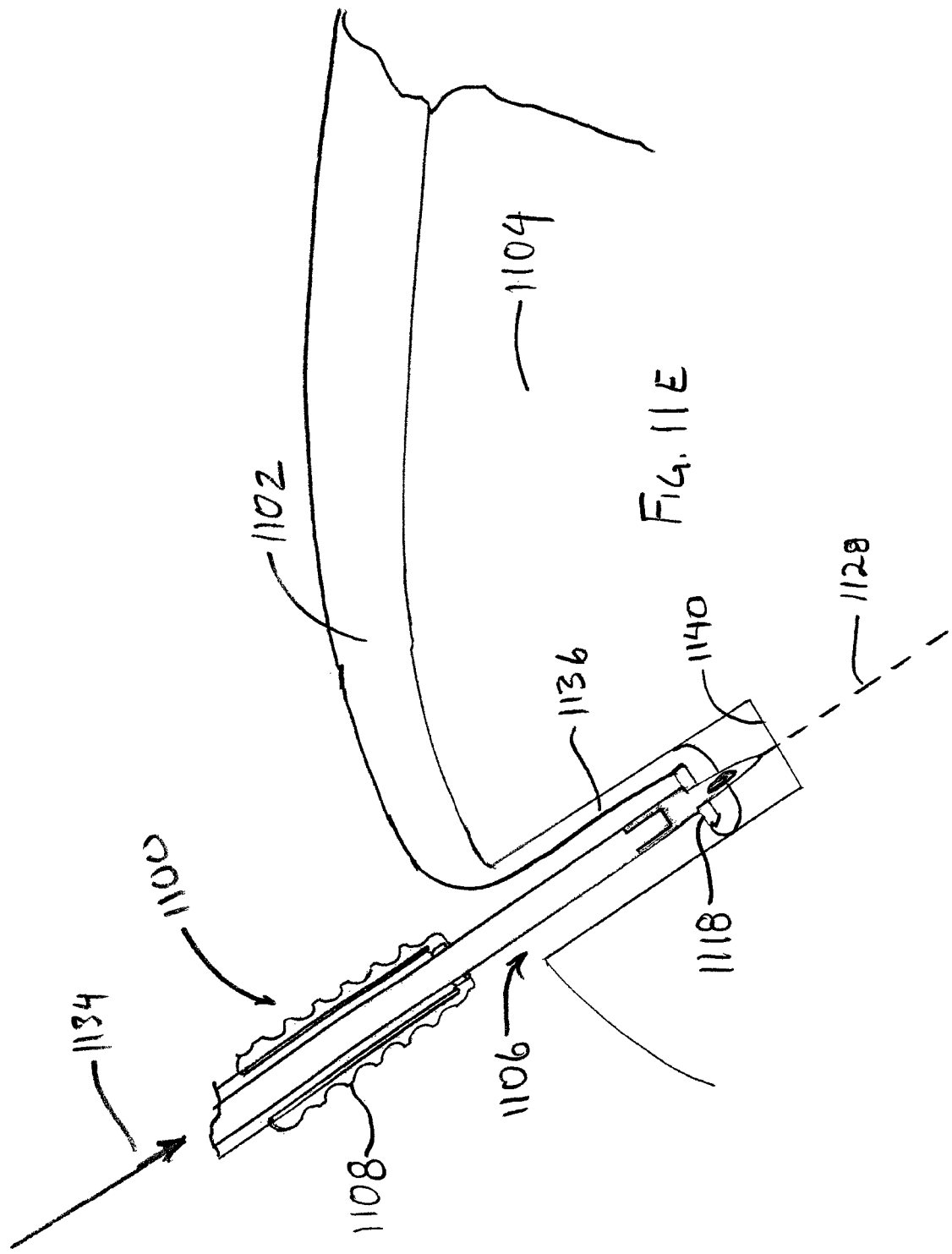

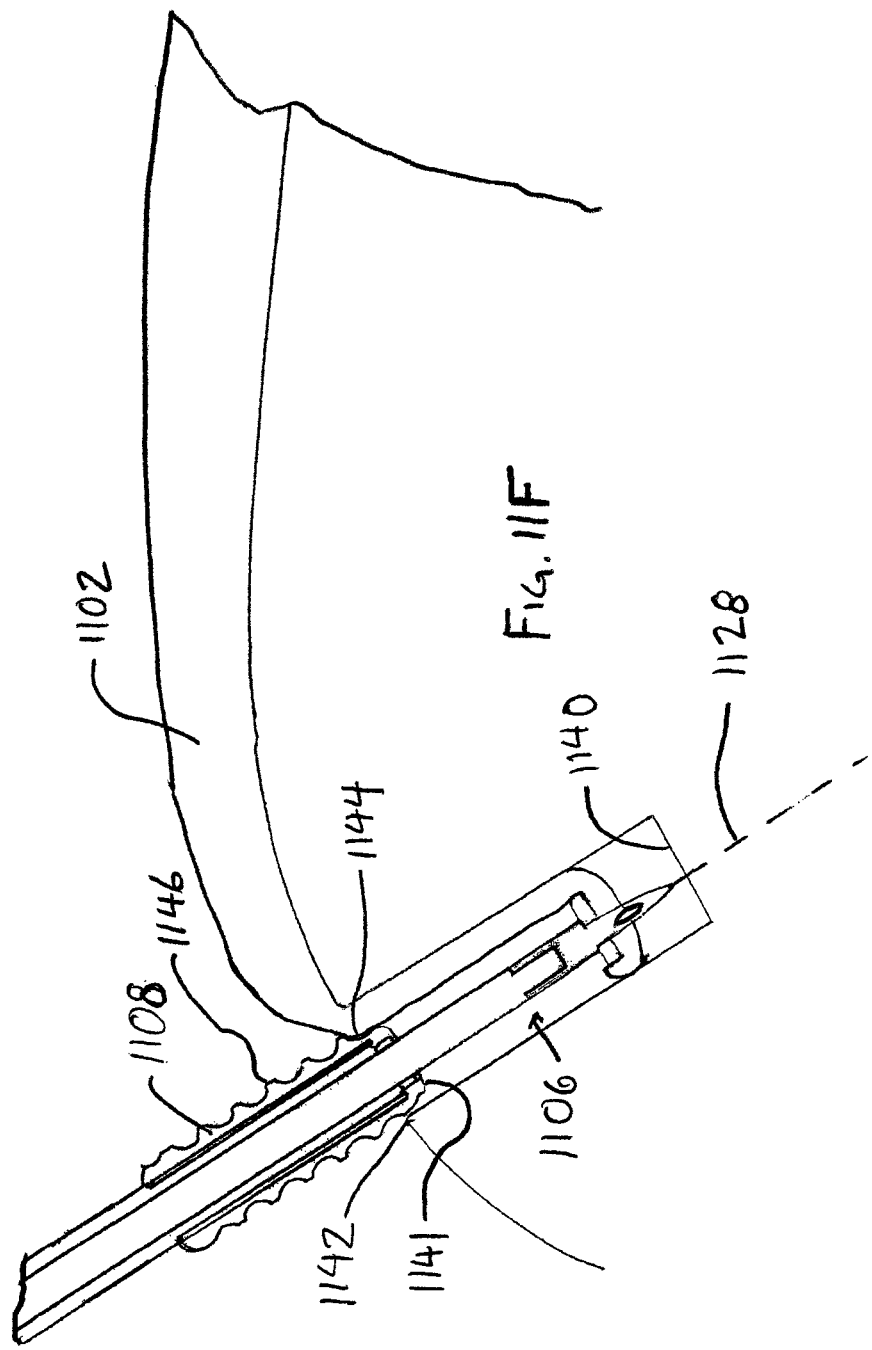

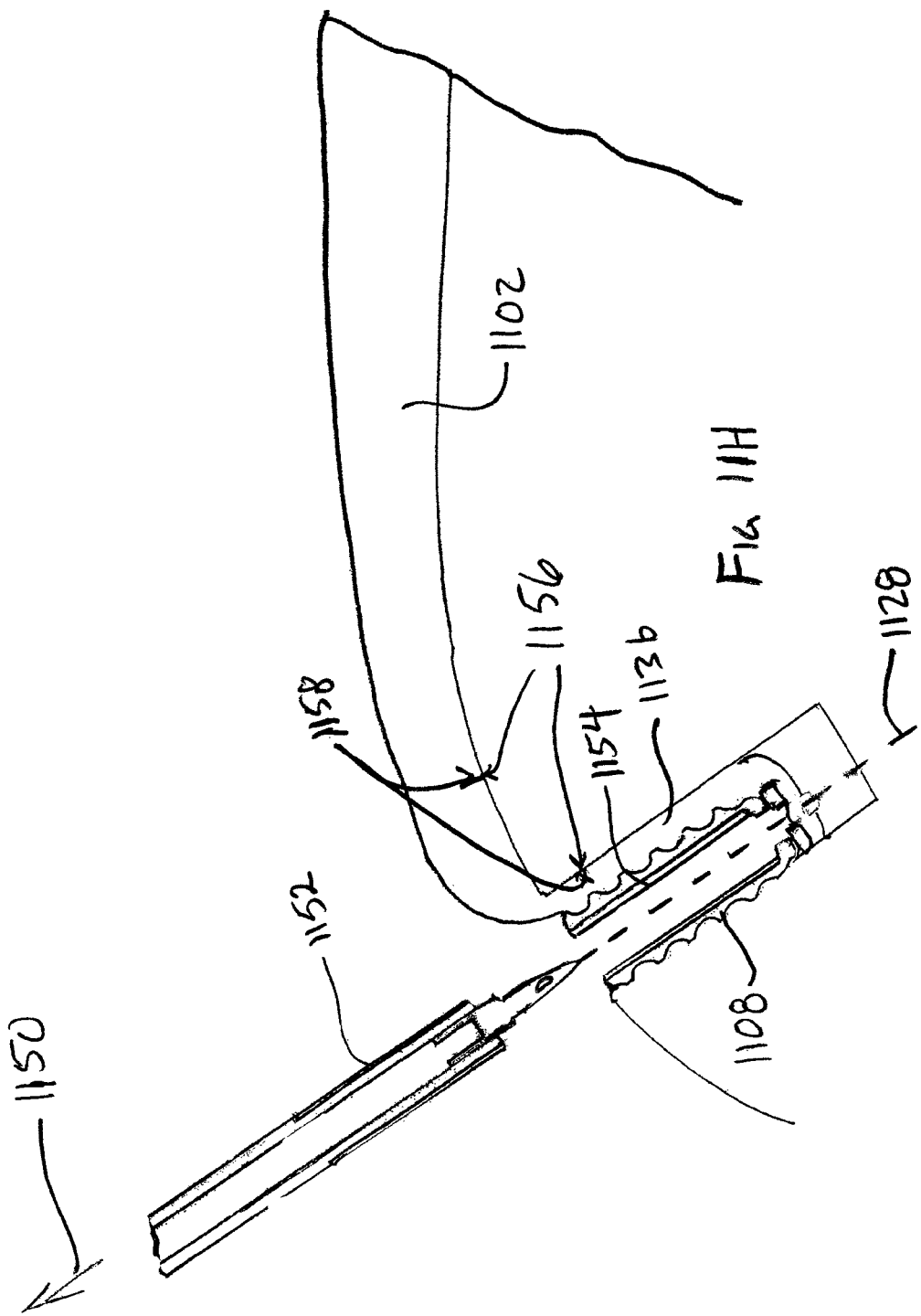

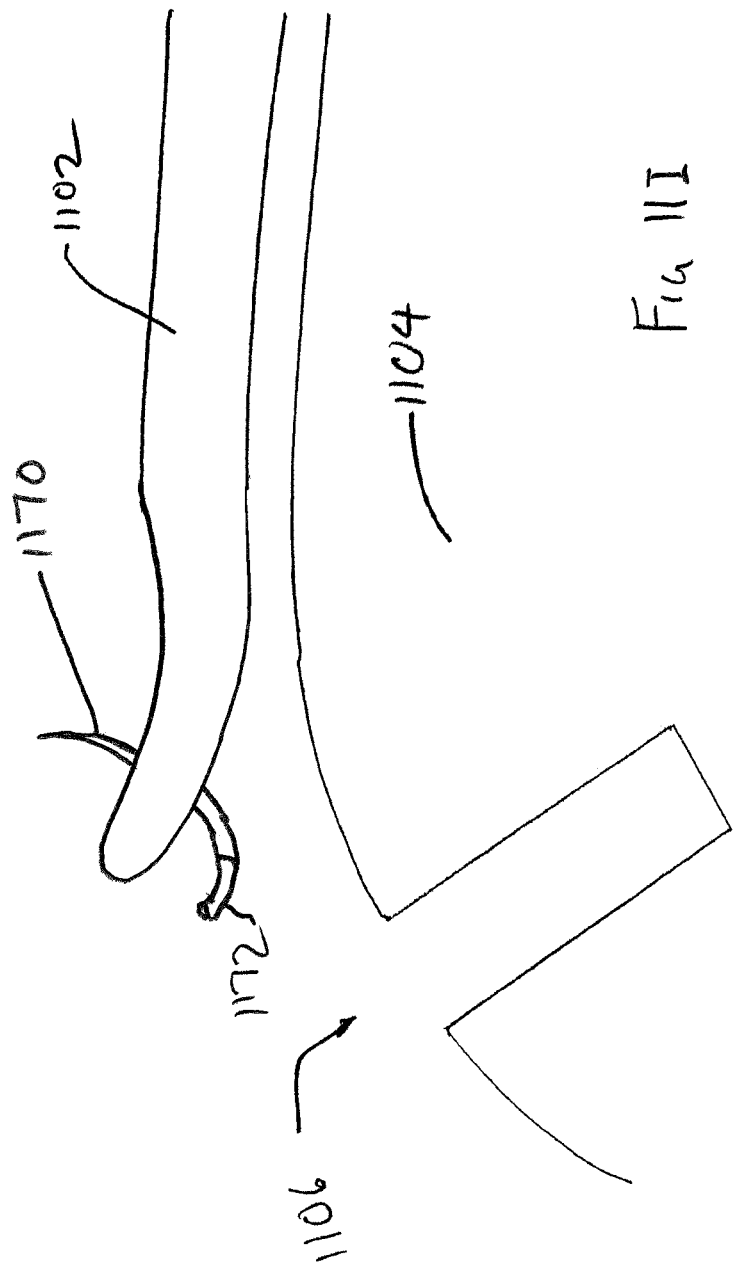

SURGICAL TOOL AND METHOD OF USE

CROSS-REFERENCE TO RELATED APPLICATIONS

This application is a continuation of U.S. patent application Ser. No. 16/551,705 filed on Aug. 26, 2019 which, in turn claims benefit of U.S. provisional patent application No. 62/724,599 filed on Aug. 29, 2018, and claims benefit of U.S. provisional patent application No. 62/722,976 filed on Aug. 26, 2018; and the present application is a continuation of U.S. patent application Ser. No. 16/551,705 filed on Aug. 26, 2019 which, in turn is a continuation-in-part of U.S. patent application Ser. No. 16/206,736 filed on Nov. 30, 2018 which, in turn, is a continuation of international patent application PCT/US 2017/035792 having an international filing date of Jun. 2, 2017 and which PCT application claims benefit of U.S. provisional patent application 62/344,489, filed on Jun. 2, 2016, and which PCT application claims benefit of U.S. provisional patent application 62/368,023 filed on Jul. 28, 2016, the disclosures of all of the foregoing being herewith incorporated by reference in their entirety.

FIELD OF THE INVENTION

The present invention relates to a system, method and apparatus for fixturing tissue and, more specifically, to adjustable surgical tenodesis fixturing.

SUMMARY

A wide variety of traumatic injuries can result in detachment of ligament and/or tendon from bone. In such circumstances, surgical reattachment offers the potential for substantial recovery. Generally, reattachment surgery involves fixing a portion of the detached soft tissue, e.g., ligament, tendon, to a relatively hard substrate such as bone. The soft tissue is typically placed in contact with a surface of the substrate at, or adjacent to, the point of detachment and mechanical fixation is applied to hold the respective tissues in contact with one another while healing takes place.

Reattachment surgery can be accomplished both by open methods and arthroscopically, and a variety of systems and techniques exist to effect the necessary tissue fixation. Regardless of the approach taken, however, precision of positional and tension control of the tissues involved, and of any sutures used for placement and fixation, can have a significant impact on achieving favorable outcomes. It is also beneficial to simplify procedures wherever possible, reducing time and personnel involved in the operation. The benefits to the patient of reducing time of a procedure are widely known and the economic impact of having an equally effective or better procedure performed in less time and/or by fewer medical personnel is increasingly significant.

Through experience, careful analysis and creative effort, the inventors of the present invention have identified an opportunity to provide for tissue fixation and developed novel improved systems methods and apparatus.

Achieving appropriate position and tension in the graft can be difficult in practice. Existing techniques include the fixation of suture to bone using threaded or barbed anchors and coupling the suture to soft tissue using surgical knots or knotless fixation. In the case of knotless fixation, a suture maybe captured by an interference fit between a suture anchor and a region of surrounding bone. In other techniques, soft tissue is drawn into a prepared aperture in the adjacent substrate and pinned against a surface of that substrate by interference with a surface region of an anchor.

In certain procedures, once soft tissue has been attached to the suture, a distal end of the suture can be positioned so as to properly locate the soft tissue with respect to the bone. Thereafter, a fixturing mechanism can be applied to ensure that this relationship is maintained. Preferably, the process will account for the fact that application of the fixturing mechanism may tend to change the position and/or tension of a portion of the suture material.

The present invention includes an integrated surgical tool including an anchor driver and a guide portion. The guide portion is arranged to allow a user to position first and second materials (e.g. bone, soft tissue or synthetic tissue or a device) in relation to one another and then release the anchor driver so as to allow engagement of the anchor driver with one or more of the tissues and fixate the tissues together (e.g. ligament or tendon to bone). Depending on the particular arrangement of the surgical tool, the surgical tool will include a suture guide that positions a suture within a prepared bore of a substrate bone material. The suture, having been attached to a soft tissue or material, is then fixed in place with respect to the bone by releasing the anchor driver portion and allowing a bone anchor coupled to the anchor driver to be fully engaged with the substrate bone material.

In other embodiments, direct tissue fixation for example, soft tissue will be directly positioned and held in place by a guide portion of the surgical tool. Once the soft tissue is positioned, an anchor guide is released and the anchor (anchor, suture anchor, soft tissue anchor, threaded device or driven in device) directly engages both the soft tissue and underlying bone tissue to achieve effective fixation of the two materials.

Thus, in certain embodiments, the invention includes a surgical tool that incorporates a suture guide and anchor driver supporting an anchor where the anchor is maintained at a distance from the suture guide until release of a detent mechanism. Thereafter, the anchor is allowed to move into proximity to the suture guide, fixing a suture supported by the suture guide to a substrate, the entire procedure being achievable with a single hand. In certain embodiments, the invention includes a surgical tool comprising, a handle portion, said handle portion including a detent mechanism, a tissue positioning portion, said tissue positioning portion being releasably coupled to said handle portion through said detent mechanism; and a substrate anchor driver portion, said substrate anchor driver portion including a coupling feature for coupling said substrate anchor driver portion to a substrate anchor, wherein said handle portion, said tissue positioning portion and said substrate anchor driver portion share a mutual longitudinal axis, and wherein said tissue positioning portion and said substrate anchor driver portion are disposed in controlled sliding relation to one another, subject to operation of said detent mechanism.

In certain embodiments the invention includes a non-cannular or cannular handle portion containing a push or sliding type button that is designed to allow or prevent rotation and axial movement of an inner shaft that is housed within an outer shaft, such that the inner shaft can rotate and collapse within the length of an outer shaft.

The inner shaft has one or more detents, that the button described above can control, that allows the inner shaft to be fixed at one or more points along its length. Additionally, the inner shaft has a distal tip that has an integral or detachable elongated eyelet that can accommodate one or more length(s) of suture.

In certain embodiments, the eyelet is oval shaped and designed to place the suture at an effective depth within a socket or tunnel in bone. The tip is designed to collapse within the cannulation of an implant made of metal, polymer or other biocompatibly suitable material and release the suture captured by the eyelet in its original condition.

In certain embodiments, the eyelet is arranged to collapse as the anchor is screwed into the bone. The collapse of the eyelet releases the suture and allows the inner shaft to be extracted from the implant. The outer shaft has a proximal end that is fixed within the handle and a distal end that has a drive mechanism with a geometric shape designed to either advance a cannular implant that has threads that allow it to be turned in the prepared boney socket or tunnel, or of another type that allows the implant to be driven into the prepared socket or tunnel. Both designs, and others described herewith, are purposed to capture and secure one or more sutures against its length and the socket or tunnel.

Screwing or driving in the cannular implant into bone provides the necessary mechanism to place and hold tissue into the desired position. The features of this design allow the user to place, tension and fix tissue to a boney surface. Unlike other designs, the user is not required to use two hands to deploy the anchor, freeing the other hand to assist in other aspects of the procedure.

In still further embodiments, the driving apparatus is prepared as described above. However, instead of an eyelet on the inner shaft, the apparatus features a polymer, or other suitable biocompatible material, washer designed to be releasably fastened to an inner shaft, which is inserted into soft tissue, e.g. biceps tendon.

The washer serves to increase the surface area of the inner shaft and help to prevent the tip from passing through the tissue further than desired. Upon achieving the desired fixation described below, the inner shaft and outer shafts are extracted from the patient, leaving the washer trapped between the soft tissue and the tip of the fixation screw.

Another iteration of the device includes an inner shaft that in addition to accommodating the washer above, includes an inner shaft with a slot or eyelet that allows the user to pass a suture or sutures through the soft tissue and then pass the free ends of the suture through the eyelet or slot.

Once this step is completed, the user has the soft tissue firmly attached to the device. This step adds improved ability to control and manipulate the soft tissue. Like the embodiments described above, the outer shaft is used to propel a threaded or push-in type anchor in a boney socket where the soft tissue has been placed. The anchor creates an interference fixation, trapping the soft tissue within the prepared socket. This design also can be used with a single hand, thus improving its utility.

In light of the disclosure presented herewith, the invention includes in certain embodiments, an implant insertion system with an implant driver. The implant driver includes a first longitudinal cannular shaft having a proximal end and a distal end. First longitudinal cannular shaft also has a first longitudinal axis defined concentrically within the shaft between the proximal end and the distal end. The cannular shaft has a coupling feature adjacent to the distal end, where the coupling feature is arranged, configured and adapted to releasably support a suture anchor. That is, in certain embodiments, a suture anchor is fixed on a releasable splined feature so that it is held in place until installed in a substrate such as bone, and then released from the splined feature as the cannular shaft is withdrawn.

The implant insertion system also includes a suture guide. The suture guide includes a further longitudinal shaft with a proximal end, a distal end, and a second longitudinal axis defined concentrically within the shaft between the proximal end and the distal end.

As the implant insertion system is assembled, the second longitudinal shaft is installed slidingly within the cannular shaft. One of skill in the art will thus appreciate that the the second longitudinal axis and the first longitudinal axis are aligned with one another. Indeed, depending on the specific configuration of the cannular shaft and the further longitudinal shaft of the suture guide, the two longitudinal axes will often be coincident—i.e., align with one another.

The implant driver also includes a suture loop feature. The suture loop feature generally includes an aperture through which a portion of a suture is threaded or otherwise inserted so that the suture loop feature controls the suture and/or is slidingly coupled to the suture. Generally, the suture loop feature is disposed at the distal end of the second longitudinal shaft. In various embodiments, the suture loop feature is integrally formed with the second longitudinal shaft. In other embodiments, the suture loop feature is prepared independently and then fasten to the distal end of the second longitudinal shaft. This fastening is accomplished with a combination of internal and external threads, with an interference fit, with a pin or dowel or other device inserted through a transverse bore spanning both the suture loop feature and a portion of the shaft, by welding the suture loop feature to the end of the shaft by, for example, resistance welding, arc welding, laser welding, soldering, brazing, or any other fastening technique that is known or becomes known in the art, or, for example, by the action of a chemical or physical adhesive such as, for example and without limitation, a polyacrylate adhesive.

In addition, in certain embodiments, the suture loop feature will be formed in situ on the end of the second longitudinal shaft by, for example, powder metallurgical and/or sintering techniques, additive manufacturing techniques such as, for example, 3D printing and/or in situ molding techniques such as, for example, metallic diecasting or polymer injection molding. It will be appreciated by one of skill in the art that the foregoing are merely exemplary of a wide variety of manufacturing techniques that will be advantageously employed depending on the particular requirements of a particular embodiment or application of the invention.

In certain embodiments, the suture loop feature includes a body portion having at least first and second surface regions, where the first and second surface regions taper towards the second longitudinal axis in proximity to a distal end of the suture loop feature. In other words, the suture loop feature will, in certain embodiments, be generally pointed, arriving at, for example, a sharp point, a rounded point, a stub point, a small flattened surface, or any other configuration that will be found advantageous in particular circumstances. A cross-section of this point will be, in certain embodiments, a generally diminishing circular cross-section. In other embodiments, this cross-section will be polygonal (i.e. any polygon between triangle and a true circle, stellate, oval, flat oval (i.e., of the form of two semicircles separated by intervening line segments) or of any other form. Moreover, in various embodiments the taper will include one or more of linear regions and nonlinear regions so as to include, e.g., conical surface regions, semi ellipsoid surface regions, etc.

In certain embodiments, the suture loop feature will include first and second circumferential edges, spanned therebetween by an internal surface region. Accordingly, the internal surface region defines an eyelet through the body portion of the suture loop feature. This eyelet, eye, or bore is arranged to receive a suture through its aperture in the manner discussed above and further illuminated below. In many embodiments, the eyelet or aperture will be generally transverse to the second longitudinal axis, so that a suture enters the eyelet on one side of the second longitudinal shaft and exits the eyelet on the other side of that shaft. As noted above, in certain embodiments, the eyelet will be oval-shaped. In other embodiments, the eyelet will be circular, polygonal, generally rectangular, or have any other configuration found to be desirable in relation to particular application and circumstance.

As will be apparent in reviewing the attached figures, in certain embodiments, the body portion of the suture loop feature includes a spine portion on one side of the eyelet and a latch portion on an opposite side of the eyelet. One of skill in the art will appreciate that this latch portion serves to releasably contain a portion of suture within the eyelet. Thus, the suture advantageously is coupled to the eyelet, and thus to the suture loop feature when desired and, thereafter, can be released from the eyelet by activation of the latch portion of the suture loop feature.

It will be appreciated that a wide variety of modes of operation will be employed in latch portions prepared according to various aspects and embodiments of the invention. Thus, in certain embodiments, the latch portion will be formed of a material that is designed to deform elastically to allow passage of the suture into and/or out of the eyelet and thereafter to resume its earlier position (i.e., effectively re-closing the eyelet once the suture portion has passed into or out of an aperture formed by displacement of the latch portion.

In other embodiments, the latch portion will be formed of a material that will tend to deform inelastically, or at least where it's elastic limit will be exceeded by operation of the latch portion. Thus, for example, in certain embodiments, a suture will be threaded through the eyelet and thereafter released from the eyelet by a substantially inelastic displacement of the latch portion. This transition will be effected, in various embodiments by, for example, pulling the eyelet away from the suture portion after the suture has been fixed in place by, for example, the installation of an anchor. In other embodiments, displacement of the latch portion, and consequently opening of the eyelet and release of the suture, takes place in response to withdrawal of the suture loop feature proximally outward through a longitudinal bore of the cannular first longitudinal shaft.

In any event, it will be appreciated that in certain embodiments of the invention, the latch portion will be arranged, configured and adapted to transition from a first state in which the eyelet is closed to a second state in which the eyelet is open. Accordingly, and as described above, in the first state the eyelet is adapted to capture a length of suture slidingly therewithin, and in the second state said eyelet is adapted to release a portion of the length of suture from the eyelet, and thus from the suture loop feature.

In certain embodiments, the implant insertion system will also include a handle. The handle can have any of a wide variety of configurations depending on the conditions of a particular application. In certain embodiments, the handle will be generally cylindrical and may be generally circularly cylindrical. Other cross-sections and configurations such as, for example, a T-handle, a pistol grip, a ball or generally spherical or ellipsoid handle, and/or a polyhedral handle, and or combinations thereof, will also be beneficially employed in corresponding embodiments.

In certain embodiments, the handle will be substantially fixedly coupled to the proximal end of the cannular implant driver shaft. Consequently, the handle will be configured, arranged and adapted to convey a manual torque applied to the handle through the first longitudinal shaft and its coupling feature to the suture anchor. In other words, by pressing and twisting on the handle, the user is able to install an exemplary suture anchor into a substrate such as bone or cartilage. Of course alternative suture anchors will also be applicable including barbed suture anchors and suture anchors with other surface features.

In certain embodiments, the implant insertion system will include a detent mechanism. The detent mechanism will generally, though not always, be disposed within the handle of the apparatus. In such embodiments, the detent mechanism is arranged and configured to constrain a sliding and/or rotational motion of the second longitudinal shaft within the cannula of the implant driver shaft. This allows a user to control a location of the suture loop feature with respect to the distal end of the first longitudinal cannular shaft. In other words, and as will be further described and illustrated below, in a first operational mode, the suture loop feature is extended distally away the suture anchor mounted on the distal end of the cannular implant driver shaft.

Beneficially, in certain embodiments, the detent mechanism will be arranged so that a surgeon or other user can use the same hand for holding the handle of the implant insertion system and for activating the detent release (e.g., by depressing a pushbutton, pulling a trigger or sliding a slider) so that, once sutures and/or tissue are properly positioned, the anchor can be advanced into the substrate bone so as to fix the suture and/or tissue in place.

It will be understood by one of skill in the art that the detent mechanism may allow the initial distance between the suture loop and the distal end of the anchor to be preset at any of variety of desirable distances.

The following description is provided to enable any person skilled in the art to make and use the disclosed inventions and sets forth the best modes presently contemplated by the inventors of carrying out their inventions. In the following description, for purposes of explanation, numerous specific details are set forth in order to provide a thorough understanding of the present invention.

It will be apparent, however, to one skilled in the art, that the present invention may be practiced without these specific details. In other instances, well-known structures and devices are shown in block diagram form in order to avoid unnecessarily obscuring the substance disclosed. These and other advantages and features of the invention will be more readily understood in relation to the following detailed description of the invention, which is provided in conjunction with the accompanying drawings.

It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art would appreciate that the figures taken together reflect various embodiments exemplifying the invention.

Correspondingly, referenced throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment"

in various places throughout the specification are not necessarily all referring to the same embodiment. Furthermore, the particular features, structures, or characteristics may be combined in any suitable manner in one or more embodiments.

BRIEF DESCRIPTION OF THE DRAWINGS

FIG. 4 shows, in schematic perspective view, certain aspects of an exemplary suture control tip prepared as a discrete component, and an associated portion of a suture guide shaft;

FIG. 11A shows, in schematic cross-sectional view, an exemplary state in an exemplary method of using a surgical tool;

FIG. 11C shows, in schematic cross-sectional view, an exemplary state in an exemplary method of using a surgical tool;

FIG. 11E shows, in schematic cross-sectional view, an exemplary state in an exemplary method of using a surgical tool;

FIG. 11F shows, in schematic cross-sectional view, an exemplary state in an exemplary method of using a surgical tool;

FIG. 11H shows, in schematic cross-sectional view, an exemplary state in an exemplary method of using a surgical tool;

FIG. 11I shows, in schematic cross-sectional view, an exemplary state in an exemplary method of using a surgical tool;

DETAILED DESCRIPTION

Figure 1:
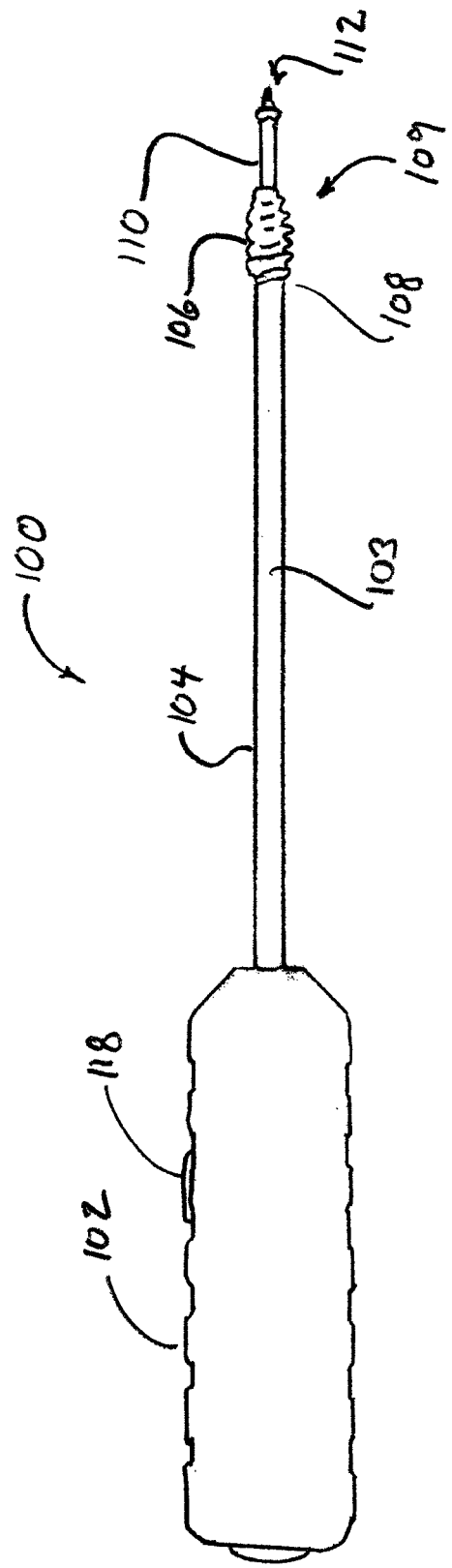
FIG. 1 shows, in schematic side elevation, an exemplary surgical apparatus prepared according to principles of the invention.

The following description is provided to enable any person skilled in the art to make and use the disclosed inventions and sets forth the best modes presently contemplated by the inventors for carrying out their inventions. In the following description, for purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the substance disclosed.

The term "proximal" as used herein refers to that end or portion which is situated closest to the user of the device, farthest away from the target surgical site. In the context of the present invention, the proximal end of the implant insertion system of the present invention includes the handle portion.

The term "distal" as used herein refers to that end or portion situated farthest away from the user of the device, closest to the target surgical site. In the context of the present invention, the distal end of the implant systems of the present invention includes an anchor and/or other components configured and adapted to fit within the pre-formed implant-receiving poor, hole or socket in the substrate.

As noted above, the results of surgery directed to reattaching soft tissue and bone are likely to be improved by increasing the accuracy of relative tissue positioning, and effectively maintaining this position once established. Moreover, to the extent that this work can be completed by a single surgeon, efficiency and effectiveness are likely to be improved. Thus, in certain aspects, the present invention include systems apparatus and methods that provide enhanced control of a suture during positioning of a graft, include a suture tool arranged and configured and adapted for one-handed operation. As further described below, the present inventors have developed new and useful apparatus and methods for achieving these and other benefits.

In a first phase of operation, a surgical tool prepared according to principles of the invention is arranged and configured to have a first portion which includes a bearing surface within a bore in a substrate osseous tissue. The bearing surface supports a portion of a suture in sliding relation. By adjusting tension on a first end of the same suture, the location of soft tissue previously coupled to a second end of the same suture can be adjusted.

Once a desirable relative configuration of tissues has been achieved, a second phase of operation of the surgical tool can be effected to drive a bone anchor into the bore, capturing a further region of the suture between the anchor and the osseous tissue and effectively fixing a spatial relationship between the soft and osseous tissues.

During the first phase of operation, the bearing surface is maintained relatively distal to the anchor, which has been preloaded on the apparatus. As the second phase of operation is entered, a detent is released allowing a separation between the bearing surface and the anchor to be reduced. The structural relationships of the apparatus, and its components, as they exist within these two phases of operation, will be further clarified in light of the following figures and description.

It should be noted that the present invention includes a surgical tool that allows single-handed deployment of a suture or interference fixed tissue. Thus, a surgeon using a single hand can insert a suture guide or captured tissue within a prepared bore in a substrate. Thereafter, without removing his or her hand from the handle of the surgical tool, the surgeon can release a detent such that an anchor having a helical thread, a barbed surface feature, a smooth surface for interference fit, or any other appropriate fixation feature, can be deployed to retain the suture and/or soft tissue at the bore. This single-handed operation offers unique benefits, allowing rapid and practical fixation of tissue with limited personnel and within the constraints of space limitations in proximity to the patient.

FIG. 1 shows, in schematic side elevation, a surgical tool 100 prepared according to principles of the invention. Surgical tool 100 includes a handle member 102. The handle member is coupled to an anchor driver 104. The anchor driver 104 is cannular in form: that is, it includes a tubular member having an external circumferential surface 103 disposed about a longitudinal axis and a longitudinal bore therethrough. In the illustrated embodiment, both the external circumferential surface, and an internal circumferential surface defining the longitudinal bore of the cannular anchor driver 104 have a generally circular cross-section. It will be appreciated by one of skill in the art, however, that alternative cross-sections for either or both of these surfaces are contemplated within the present disclosure.

An exemplary anchor, 106 is shown as engaged with a spline coupling 108 at a distal end 109 of the cannular anchor driver 104.

One of skill in the art will appreciate that in other embodiments of the invention, the anchor driver will not include any spline feature, but will include other features or arrangements for coupling to the anchor. Thus, in certain embodiments, the anchor driver and anchor will have complementary helical threads. In still other embodiments, the anchor driver and anchor will have substantially smooth surfaces retained adjacent to one another by an interference fit. In still other embodiments, an adhesive material will retain the anchor driver and anchor in temporary connection to one another.

A suture guide shaft 110 is disposed coaxially within a longitudinal bore of the anchor driver 104. A distal end 109 of the suture guide shaft 110 includes a suture guide assembly 112.

Figure 2:
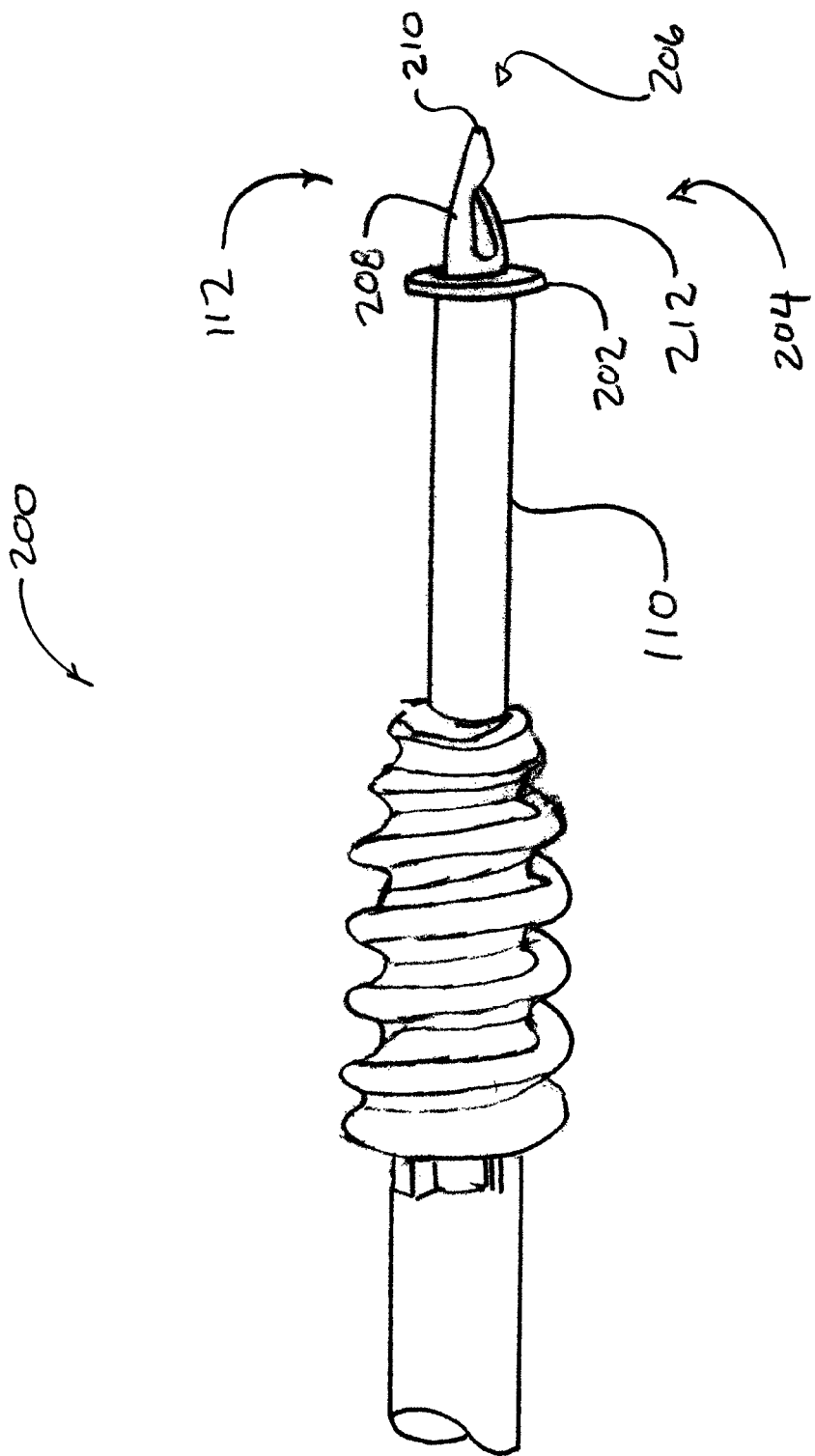
FIG. 2 shows, in schematic perspective view, a portion of an exemplary surgical apparatus prepared according to principles of the invention.

FIG. 2 shows a detailed view 200 of the suture guide shaft 110 and suture guide assembly 112 of FIG. 1. In the illustrated embodiment, the suture guide assembly 112 includes a washer 202 supported on a shoulder surface region (not visible) of the suture guide shaft 110 and a suture guide feature 204 integrally formed on a distal end 206 of the suture guide shaft 110. The suture guide feature 204 includes a spine portion 208 disposed between a nose portion 210 and the shoulder surface region of suture guide shaft 110. The suture guide feature 204 also includes a gate portion 212.

Figure 3A:
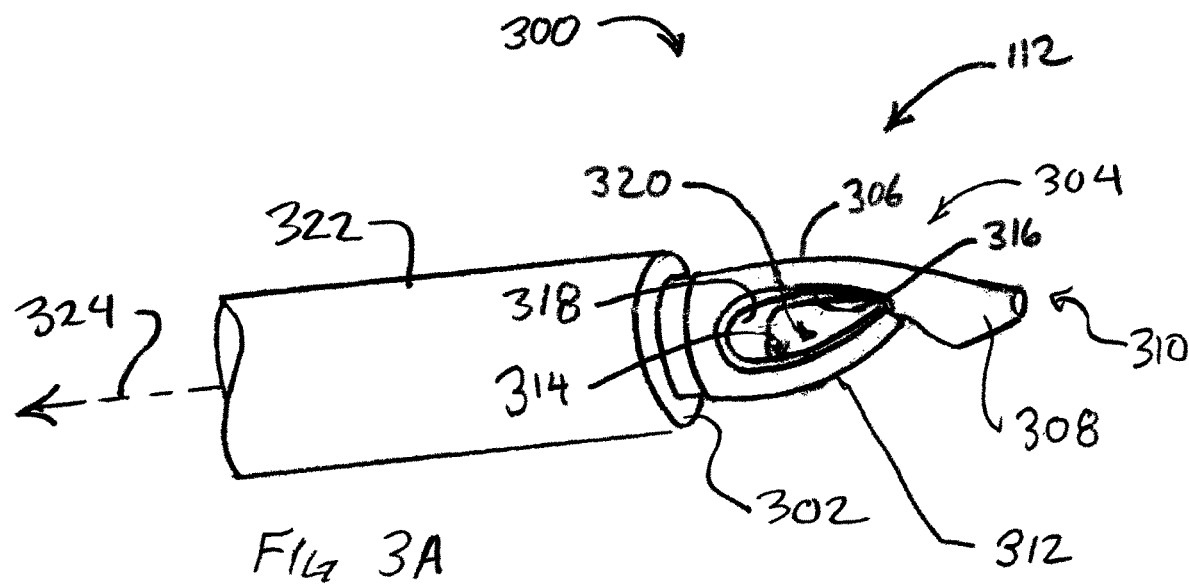
FIG. 3A shows, in schematic perspective view, an exemplary suture control tip of a surgical apparatus according to the invention in a first close mode of operation.

FIG. 3A shows a further detailed view 300 of the suture guide assembly 112 of FIGS. 1 and 2 in a closed configuration. In this illustration, the shoulder surface region 302 is clearly visible. As discussed above, this shoulder surface region 302 is well adapted to support a washer (not shown).

It will be understood by one of skill in the art, however, that other embodiments of the invention will not include the washer and still further embodiments of the invention will have no shoulder surface region.

In the embodiment illustrated, the suture guide feature 304 includes a spine portion 306 disposed between the shoulder surface region 302 and a nose portion 308. As shown, the nose portion is disposed at a distal end 310 of the suture guide feature 304.

A gate portion 312 of the suture guide feature 304, includes an internal surface region 314. Internal surface region 314 is disposed in generally spaced relation to a corresponding internal surface region 316 of the spine portion 306.

In the illustrated configuration of FIG. 3A, the gate portion is disposed in an inward-deflected arrangement so that a generally closed internal surface 318 is formed by internal surface region 314, internal surface region 316, and the intervening surface regions. It is readily apparent that the internal surface region 318 defines an aperture 320 of the suture guide assembly 112. One of skill in the art will readily appreciate that this aperture 320 is closed, and therefore adapted to contain a portion of a suture therewithin so that the suture (not shown) and suture guide feature 304 are mutually coupled to one another.

Figure 3B:
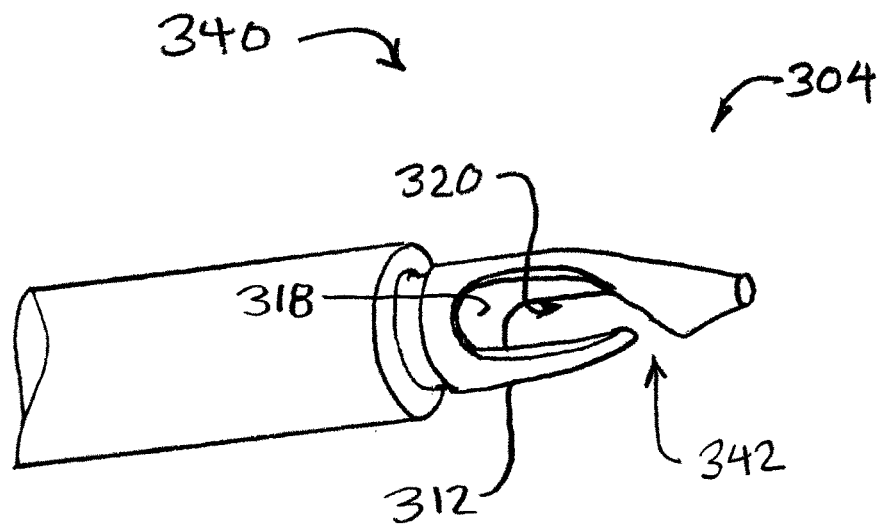
FIG. 3B shows, in schematic perspective view, an exemplary suture control tip of a surgical apparatus according to the invention in a second open mode of operation.

In contrast, FIG. 3B shows a further detailed view 340 corresponding to detailed view 300 of FIG. 3A, except that gate portion 312 of the suture guide feature 304 is disposed in an outward-deflected arrangement. Consequently internal surface region 318 is not contiguous, but open 342 at a distal end of aperture 320. Therefore, aperture 320 is open and will allow the release of any suture disposed therewithin, such that the suture guide feature 304 and the suture (not shown) are decoupled. Accordingly, as will be understood by one of skill in the art, the suture guide may be retracted once the suture has been fixed in place.

A method of using the suture guide assembly of FIGS. 1, 2 and 3 will be readily understood by one of skill in the art upon review of the further descriptions and figures provided below in relation to someone different embodiments of the invention. In particular, it will be well understood that the present invention is well adapted to use in positioning and fixing tissue to a substrate such as bone or cartilage employing a suture, as shown, for example, in FIGS. 5A-6 below. The same arrangement, optionally including a washer such as washer 202, will be employed in fixturing tissue directly to a substrate as shown, for example, in FIGS. 10A-11H below.

In certain embodiments of the invention, the gate portion 312 of the suture guide feature 304 will be urged to transition from the closed configuration of FIG. 3A to the open configuration of FIG. 3B by tension applied to the suture, and therefore to the internal surface region 314 upon withdrawal of the suture guide shaft 322 axially 324 through a cannular shaft of an anchor driver (e.g. 104 as shown in FIG. 1).

In certain embodiments of the invention, the resulting outward motion of the gate portion 312 will be a temporary transition. That is, if the gate portion is formed of a generally elastic material, and if the elastic limit of the gate portion material is not surpassed, the gate portion will tend to return to the closed configuration of FIG. 3A, after the suture portion has been released.

In other embodiments of the invention, the outward passage of the suture material will tend to exceed the elastic limit of the gate portion material and thus permanently deform the gate portion such that the gate portion will tend to remain in the configuration of FIG. 3B as the suture guide shaft 322 is withdrawn.

Accordingly, it will be appreciated by one of skill in the art that various embodiments of the invention will include a variety of materials having a corresponding variety of elastic limits, tensile and compressive strength, chemical characteristics and other features chosen for optimal performance when employed in a particular application of the present invention. In particular, it will be appreciated that in certain embodiments, washer 202 of FIG. 2 will include a poly-ether-ether-ketone (PEEK) material. In other embodiments of the invention, washer 202 will include one or more of titanium and stainless steel.

More generally, it will be appreciated that any portion of an embodiment of the present invention will, as appropriate, include one or more of natural and synthetic polymers including, for example, poly-ether-ether-ketone (PEEK); reinforced polymer materials including reinforcing sheets, particles and fibers of, for example, one or more of, carbon fibers, carbon nano-materials, glass fibers and metallic fibers; precious metals, stainless steel, titanium and other metals; porcelain, alumina and other ceramics including, for example, aluminum oxide, calcium oxide, calcium phosphate hydroxyapatite, and zirconium.

In addition, it will be appreciated that while gate portion 312 of the invention embodiments shown in FIG. 3 is integrally formed of the more or less elastic or inelastic material of suture guide shaft 322, in other embodiments, the gate portion will be formed as a discrete component.

In still other embodiments, the gate portion 312 will be formed of a shape-memory alloy of any appropriate composition now known or yet to be discovered in the art, that allows the gate portion 312 to desirably transition from the closed configuration of FIG. 3A to the open configuration of FIG. 3B in response to a change in temperature of the apparatus. This change in temperature may occur according to a changing environment of the apparatus, or may occur in response to, for example, a heating or cooling element disposed in direct or indirect thermal contact with the gate portion 312.

FIG. 4 shows a still further embodiment 400 of the invention in which the suture guide portion 402 is formed as a discrete element. In the illustrated exemplary embodiment, suture guide 402 includes a coupling portion 404. As shown, coupling portion 404 includes an externally threaded portion 406 adapted to be threadingly coupled to a corresponding internally threaded bore 408 of a suture guide shaft 410.

In other embodiments of the invention, the gate portion 412 (or 312, as shown in FIGS. 3A and 3B) is prepared including a discrete component, as opposed to an integrally formed portion. In certain embodiments, a discrete elastic element, e.g., a coil spring or a leaf spring, is disposed and configured to urge the gate portion into the closed configuration illustrated in FIG. 3A.

Referring again to FIG. 1, and as will be further discussed below, a longitudinal displacement of suture guide shaft 110 with respect to the cannular anchor driver 104 is controlled, in part, by a suture guide release button 118.

Figure 5A:
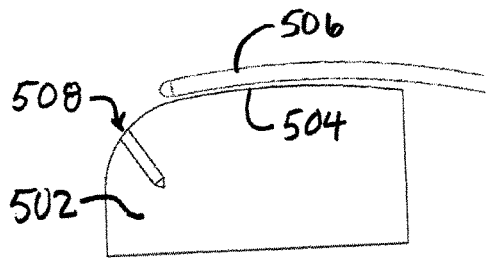
FIG. 5A illustrates a selected state of an exemplary method of employing a surgical tool prepared according to principles of the invention.

FIG. 5A-FIG. 5E illustrate selected states of an exemplary method of employing a surgical tool prepared according to principles of the invention. FIG. 5A shows, in schematic form, a portion of a bone or other substrate medium 502. Adjacent a surface region 504 of the bone 502 is a portion of a detached ligament 506. In anticipation of reattachment of the ligament, a bore 508 has been drilled through surface region 504 and into the substrate bone 502.

Figure 5B:
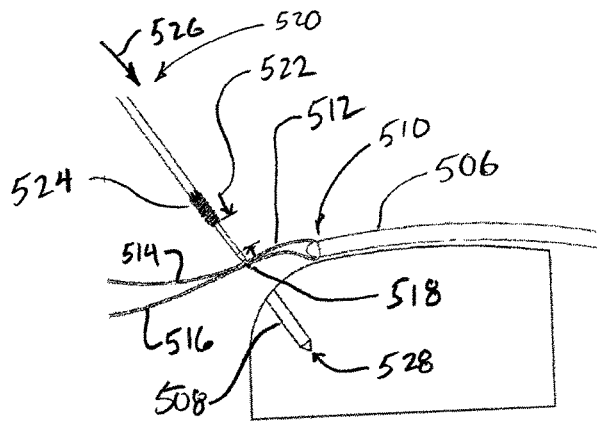
FIG. 5B illustrates a selected state of an exemplary method of employing a surgical tool prepared according to principles of the invention.

Referring to FIG. 5B, in preparation for reattachment, the ligament 506 is pierced 510 and a suture 512 is drawn through the ligament as shown. Two portions of the suture 514, 516 are disposed through an aperture (e.g., 320 of FIG. 3) of a suture guide 518, the suture guide being disposed at a distal end of a surgical tool 520.

Figure 10A:
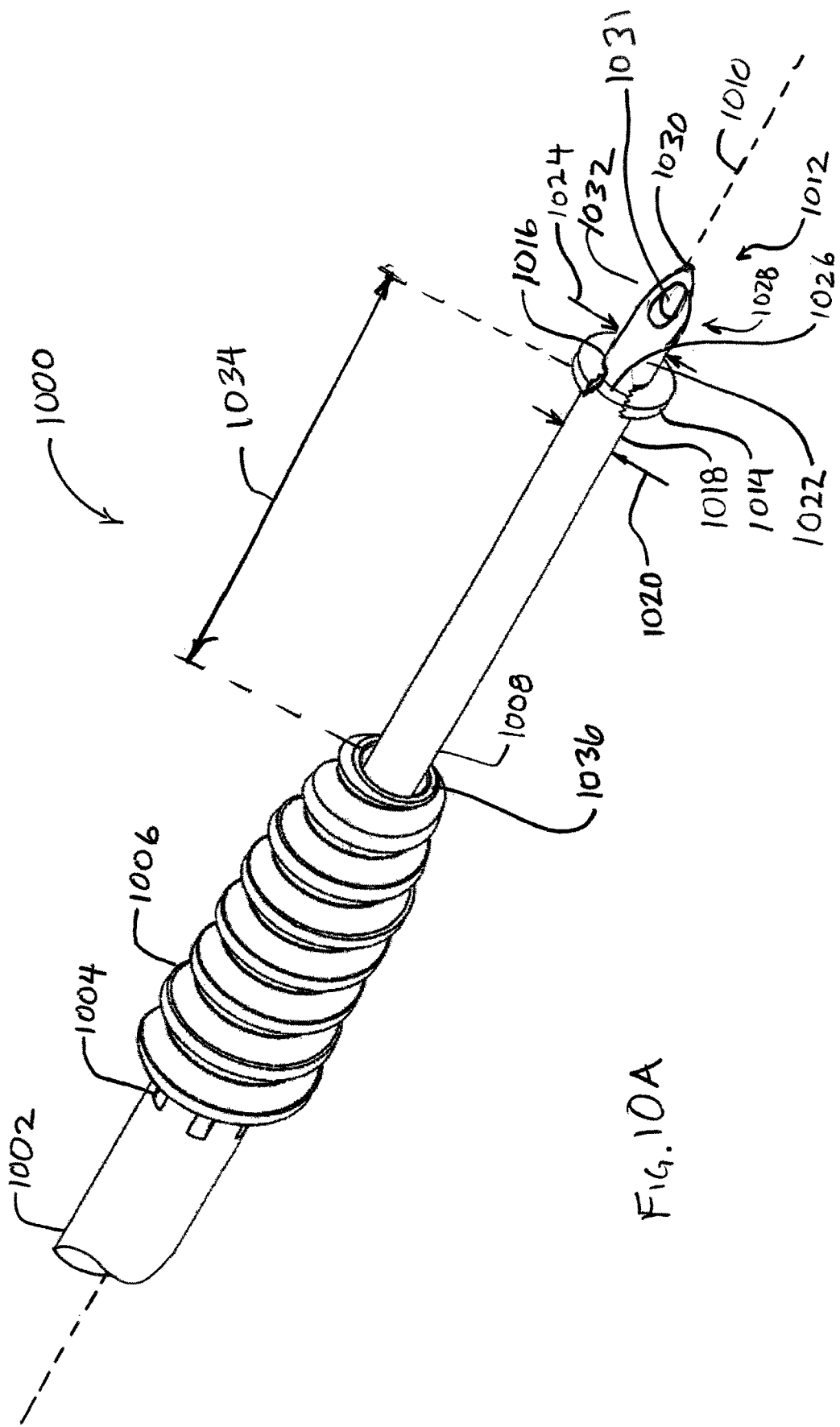
FIG. 10A shows, in cutaway perspective view, a further surgical tool prepared according to principles of the invention in an extended configuration.

As illustrated, the surgical tool 520 is configured in an extended configuration (consistent with the arrangement illustrated in FIG. 10A). Consequently a distance 522 between the suture guide 518 and a distal end of a bone anchor 524 is relatively long. Moreover, while the suture anchor is readily rotated about a longitudinal axis with respect to the bone anchor 524, distance 522 is substantially (though temporarily) fixed.

Consequently, applying a longitudinal force 526 to the surgical tool 520 tends to urge the suture guide 518 into the bore 508 and towards a distal end thereof 528.

Figure 5C:
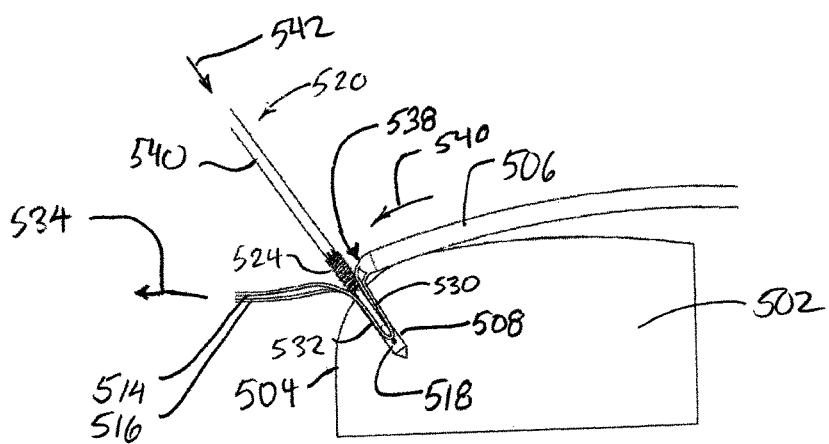
FIG. 5C illustrates a selected state of an exemplary method of employing a surgical tool prepared according to principles of the invention.

As illustrated in FIG. 5C, because the suture portions 514, 516 are disposed through the aperture of the suture guide 518, urging the suture guide 518 into bore 508 tends to draw corresponding regions 530, 532 of the suture into the bore 508. Concurrently, this motion of the surgical tool 520 brings the distal end of bone anchor 524 adjacent the surface region 504 of the bone at the mouth of the bore 508 where it passes through that surface region. By maintaining tension 534 on the suture portions 514, 516 on the side of the suture guide 518 opposite to the ligament 506, this motion can further cause a proximal end 538 of the ligament 506 to be displaced 540 towards the mouth of the bore.

By manipulation of tension 534 on the suture portions, and consequent adjustment of the position of the longitudinal suture with respect to the suture anchor, accurate and effective positioning of the ligament 506 with respect to the surface 504 of the bone 502 can be achieved. Moreover, this can be accomplished by a single individual using two hands.

That same individual, without assistance and using a single hand, can then press the release button (element 118, FIG. 1) and release the detent controlled by the release button while concurrently rotating a handle of the surgical tool 520. Rotation of the handle, which is rotationally fixed with respect to the cannular anchor driver 540, and therefore with respect to the bone anchor 524, causes a corresponding rotation of the bone anchor 524. By combining this rotational motion with an application of longitudinal force 542 external helical threads on the bone anchor 524 can be made to engage with the internal surface of bore 508 and thereby advance the bone anchor 524 into the bore 508.

One of skill in the art will appreciate that, while a bone anchor 524, exhibiting external helical threads is shown for illustrative purposes in FIGS. 5A-5E, other anchors known in the art, or that may become known in the art, may likewise be applied within the scope of the invention. Thus, for example, a barbed anchor, rather than a threaded anchor may be employed. In addition, an anchor may be employed that incorporates neither threads nor barbs, but is fixed within a bore by, for example, an interference fit. Likewise, an elastic retainer, an adhesively retained stopper, or any other retaining device appropriate to the particular circumstances will be applied and considered to be within the scope of the invention.

Figure 5D:
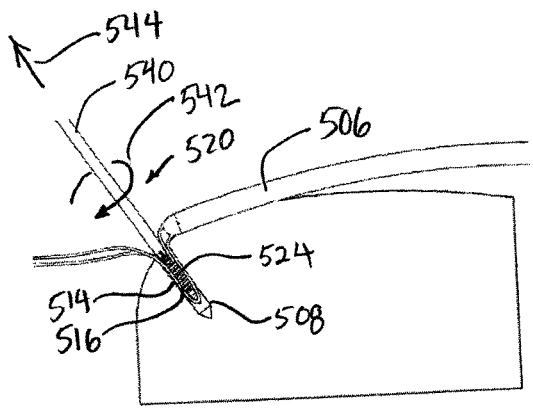
FIG. 5D illustrates a selected state of an exemplary method of employing a surgical tool prepared according to principles of the invention.

As illustrated in FIG. 5D, further rotation 542 of the cannular anchor driver 540 causes the bone anchor 524 to be fully driven into the bore 508. This tends to trap the suture portions 514, 516 firmly against respective internal surface regions of the bore 508, thereby preventing displacement of the ligament 506. Once driving of the bone anchor 524 is complete, tension may be applied 544 to the surgical tool 520.

Figure 5E:
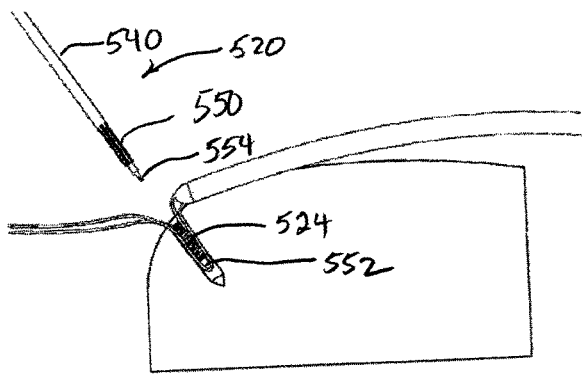
FIG. 5E illustrates a selected state of an exemplary method of employing a surgical tool prepared according to principles of the invention.

Referring to FIG. 5E, one sees that this tension results in the spline feature 550 of the cannular anchor driver 540 disengage from the bone anchor 524 and allow the surgical tool 520 to be withdrawn. As the tool is withdrawn, a portion of the suture 552 previously disposed within the eyelet 554 of the suture guide (suture loop) passes through an opening in the eyelet of the suture loop formed by operation of the gate portion of the suture loop feature. This allows the suture guide to release the suture portion 552 and permits the withdrawal of the surgical tool 520 described above.

Figure 6:
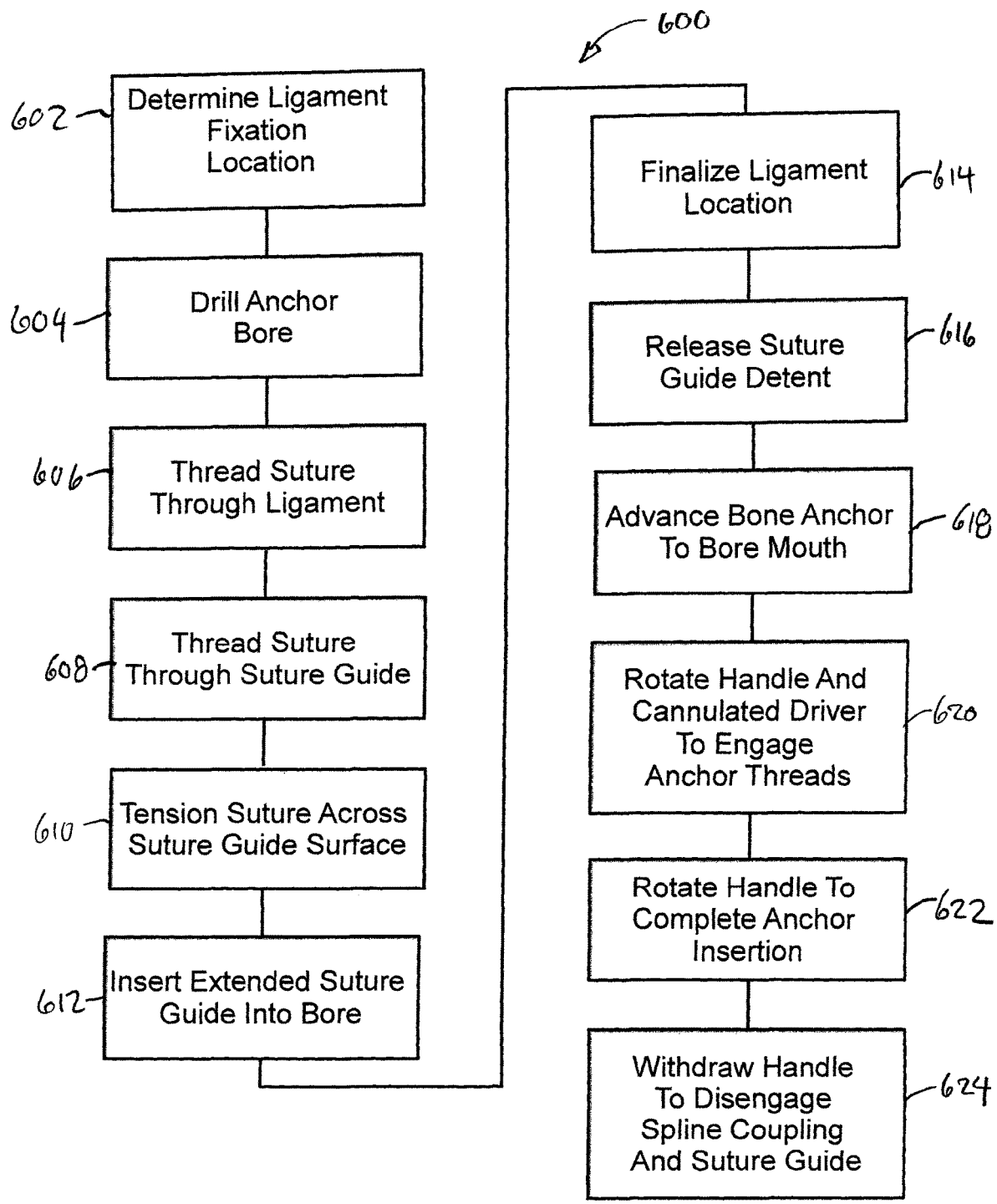
FIG. 6 shows, in flowchart form, certain portions of a method for using a surgical tool according to principles of the invention.

FIG. 6 shows, in flowchart form, certain portions of a method 600 for using a surgical tool according to principles of the invention. In the illustrated embodiment, the method includes determining a ligament fixation location 602 with respect to an underlying substrate such as bone and drilling an anchor bore in the bone 604 to receive a bone anchor and a length of suture. A length of suture is coupled to a ligament or other soft tissue by, for example, threading through the tissue with a needle 606. A portion of the suture is coupled to a suture guide by, for example, threading the suture through an aperture of a generally toroidal region the suture guide 608.

The suture guide and suture are manipulated, with the application of appropriate pressure and tension (as would be understood by one of skill in the art) to insert the extended suture guide 612 into the bore drilled at step 604. Further application of pressure to the suture guide and tension on the suture, as well as direct manipulation of the soft tissue and underlying substrate allows finalization of the ligament location with respect to the bone 614.

While holding the suture in place, a release mechanism of the surgical tool is activated. This release mechanism releases a detent that couples the suture guide to a balance of the surgical tool 616. This release of the detent mechanism allows the surgical tool to advance a bone anchor supported by the surgical tool to be advanced 618 towards and into a mouth of the bore prepared at step 604. In certain embodiments of the invention, the bone anchor will contact the underlying bone and even be advanced by rotation or pressure into the bore before any release of the detent mechanism.

Rotation of a handle of the surgical tool conveys a torque through the handle, through an anchor driver, through a spline feature and into the bone anchor so that the bone anchor threads engage an internal surface region of the bore 620. Further rotation of the handle advances the bone anchor into the bore until the anchor is fully inserted at its destination 622.

Thereafter, the handle of the surgical tool is withdrawn, disengaging the spline coupling from the now-inserted bone anchor. As the surgical tool is withdrawn, the portion of the suture that was disposed within the suture guide passes through a slot in the suture guide 624. This allows complete withdrawal of the surgical tool and leaves the suture compressed and fixed to the internal surface of the bore by the inserted bone anchor.

Figure 7:
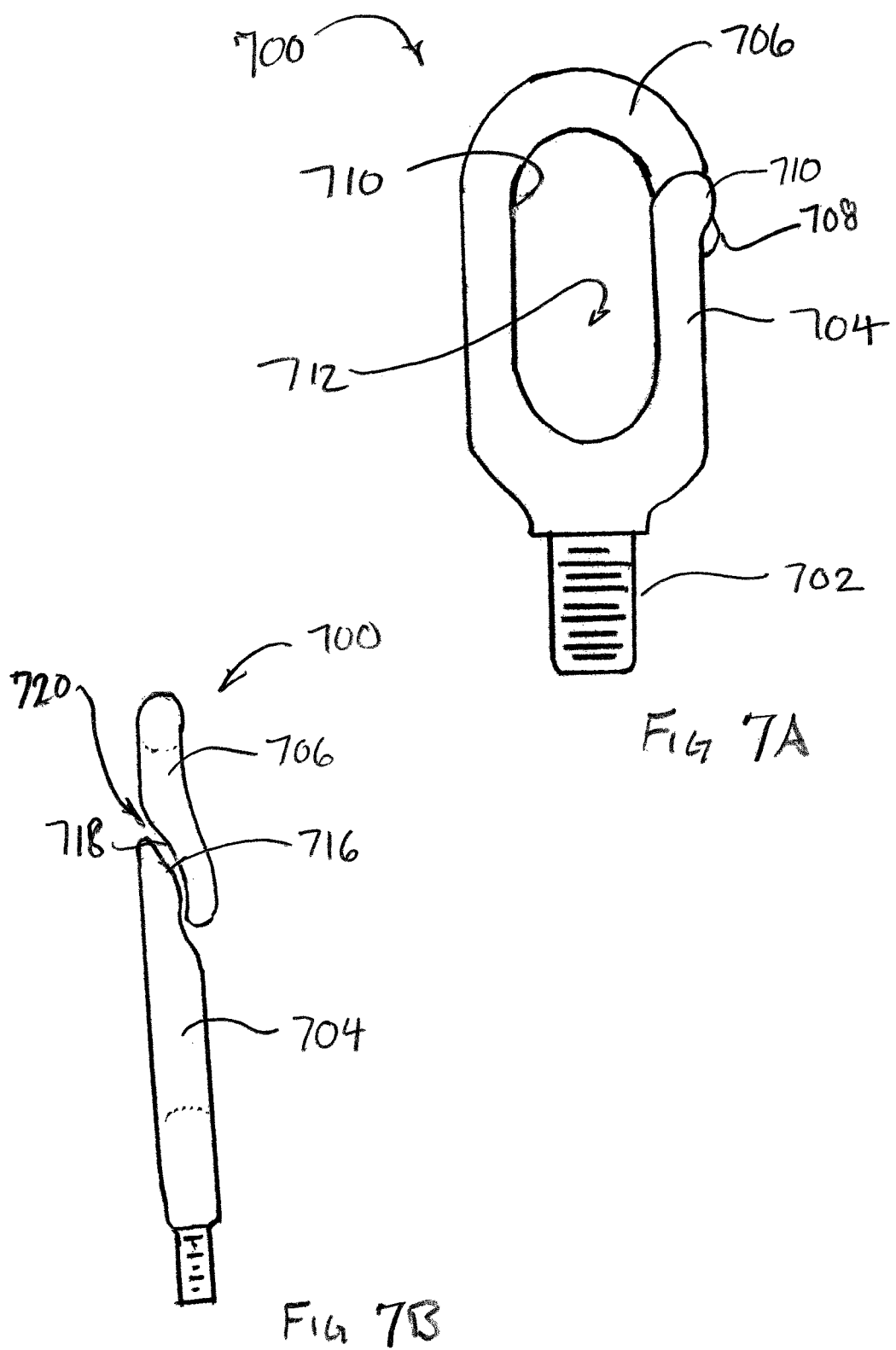
FIG. 7A shows, in schematic front elevation, a further suture loop feature for a surgical tool prepared according to principles of the invention.
FIG. 7B shows, in schematic side elevation, a further suture loop feature for a surgical tool prepared according to principles of the invention.

FIG. 7A shows, in schematic front elevation, a suture loop feature of an alternative embodiment of a suture guide prepared according to principles of the invention. Suture loop feature 700 is formed as a discrete element. It includes a coupling portion 702 that, in the illustrated embodiment, is adapted to be received into a female threaded axial receptacle at the distal end of a suture guide shaft. The suture loop portion 700 includes a spine portion 704 and a gate portion 706. An internal surface region 710 of the suture loop portion defines an eyelet 712 that is adapted to receive a portion of a suture slidingly therethrough. As will be further discussed below, and end region 708 of gate portion 706 is disposed in proximity to a further gate portion 710 of the spine portion 704, effectively closing the eyelet when the suture loop portion 700 is in a first closed state.

FIG. 7B shows, in schematic side elevation, a further aspects of the suture loop feature 700 of FIG. 7A. In particular, a portion of spine portion 704 is visible, as is a portion of gate portion 706. It will be apparent upon inspection that a first surface region 716 of the spine portion 704 is disposed adjacent to or in contact with a second surface region 718 of gate portion 706. In certain embodiments, it will be possible to load a portion of a suture into the eyelet 712 of the suture loop feature 700 by sliding the portion of the suture through a slot 720 between surfaces 716 and 718. The slot 720 is either continuously present between the two surface regions 716 and 718, or is formed by a more or less elastic displacement of the two surfaces apart from one another, either by insertion of the suture or by application of external forces (with or without a tool). Thus, a suture may be loaded into the eyelet 712 without threading and end of the suture through that eyelet.

Thereafter, the suture may be released from the eyelet by the application of further forces, as described above, that result in the elastic or inelastic displacement of the gate portion (or the spine portion). Accordingly, the suture loop portion may be withdrawn from the suture anchor site, leaving behind the suture, the anchor and the respective tissues desirably affixed to one another.

Figure 8:
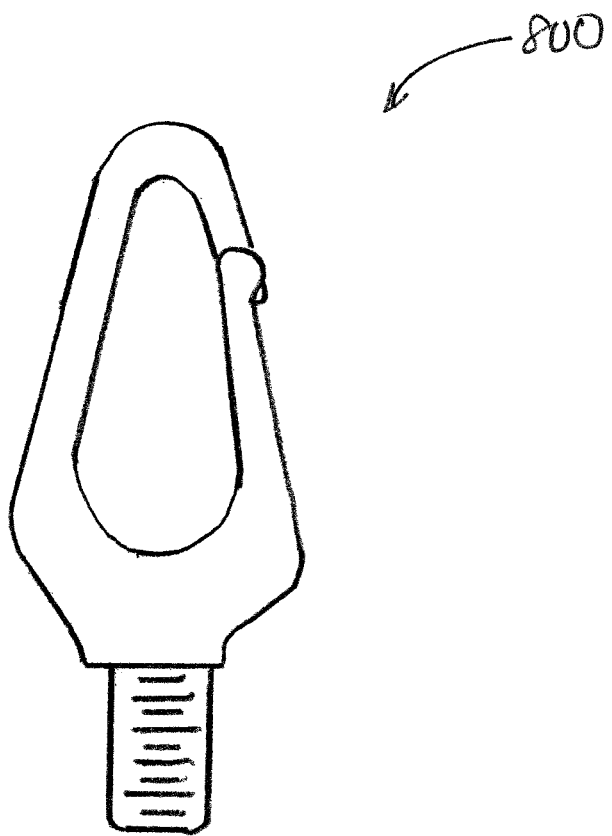
FIG. 8 shows, in schematic front elevation, a further suture loop feature for a surgical tool prepared according to principles of the invention.

FIG. 8 shows a further suture loop feature 800 that is functionally similar to that of FIGS. 7A and 7B, but having a more or less oval eyelet and a generally tapered or pointed aspect. Like the suture loop feature 700, suture loop feature 800 can be loaded with a suture without threading the suture through the eyelet.

Figure 9:
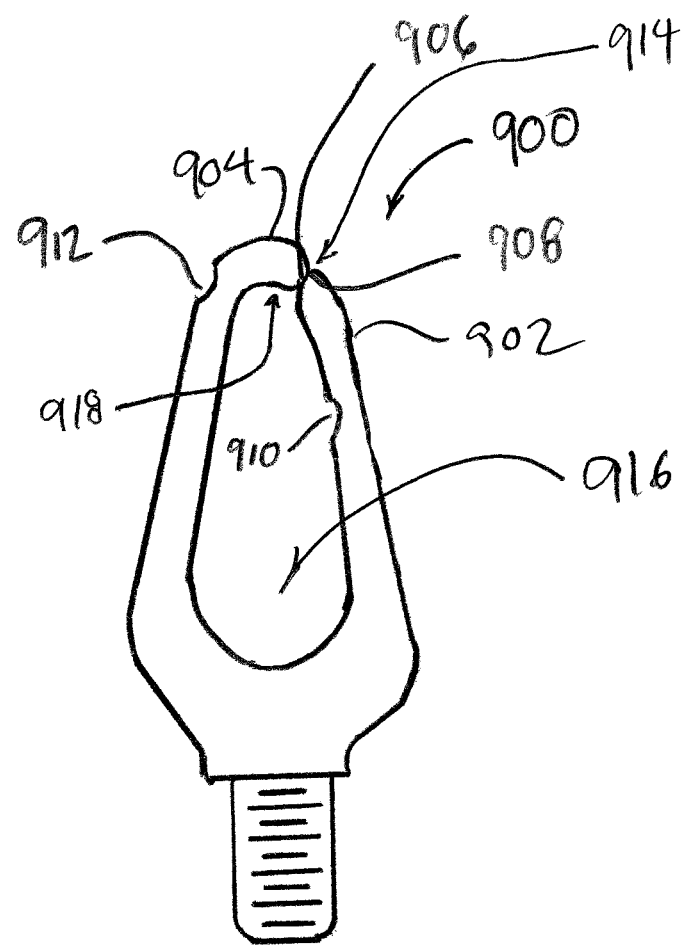
FIG. 9 shows, in schematic front elevation, a further suture loop feature for a surgical tool prepared according to principles of the invention.

FIG. 9 shows a still further suture loop feature 900. Like suture loop feature 800, suture loop feature 900 has a more or less oval eyelet and a generally tapered or pointed aspect.

In particular, suture loop feature 900 includes a spine portion 902 and a gate portion 904. Unlike the embodiments of suture loop feature 700 and suture loop feature 800, however, an interface between the spine portion 902 and the gate portion 904 includes respective end surface regions thereof 906, 908 that are butted against one another. As illustrated, respective end surface regions are curved.

In certain embodiments of the invention, respective recesses 910, 912 are provided in the spine portion 902 and gate portion 904 that increase elastic flexure in proximity to the recesses. Consequently, a portion of a suture urged inwardly in region 914 will cause flexure of the spine portion 902 so that the suture can pass into the eyelet. Similarly, outward force applied at region 918 will cause a corresponding flexure of the gate portion 904 in the vicinity of the recess 912 so that the suture can escape from the eyelet 916.

FIG. 10A shows, in cutaway perspective view, a further surgical tool 1000 prepared according to principles of the invention. Like the various embodiments described above, exemplary surgical tool 1000 includes a cannular anchor driver 1002 coupled through spline features 1004 to a bone anchor 1006. Disposed within and through a longitudinal cannula of the cannular anchor driver 1002 and the bone anchor 1006 is a shaft 1008. The shaft 1008 defines a longitudinal axis 1010.

Near a distal end 1012 of the shaft 1008, a generally toroidal bearing washer 1014 is disposed coaxially about the shaft 1008. The generally toroidal bearing washer 1014 is supported on shaft 1008 by a snug but slidable interface 1016 between an internal circumferential surface of the washer 1014 and a corresponding external circumferential surface of the shaft 1008. In certain embodiments, a cross-section of the shaft 1008 is circular. It will be appreciated, however, by one of skill in the art, that in any of the embodiments disclosed in this application, other cross-sections are contemplated to be within the scope of the invention. Such other cross-sections will include, in various embodiments and without limitation, polygonal, elliptical and otherwise arcuate cross-sections.

A first relatively proximal circumferential surface region 1018 of the shaft 1008 has a relatively large diameter 1020. A second relatively distal circumferential surface region 1022 of the shaft 1018 has a relatively small diameter 1024. A generally radial surface region 1026 disposed between surface region 1018 and surface region 1022 defines a shoulder further supporting the washer 1014 and limiting its motion in a proximal direction along longitudinal axis 1010 by mechanical interference.

In the illustrated embodiment, a distal extremity 1028 of shaft 1008 tapers to a point 1030. This taper is defined by an intermediate surface region between circumferential surface region 1022 and point 1030. An eyelet 1031, as described above, is visible adjacent the distal point 1030. In reviewing the following description as related to FIGS. 10A-11L, one of skill in the art will understand that this pointed end may be used without employing a suture and the presence of the eyelet therewithin will have no negative effect. That said, as discussed above and below in relation to short FIG. 11I-11L in certain applications and embodiments of the invention, a suture will be advantageously disposed within the eyelet to further enhance effectiveness of the inventive apparatus and system.

In various respective embodiments, this intermediate surface region includes a substantially conical surface region, an elipto-conical surface region (i.e. generally conical, but with a convex or concave surface curvature), a prismatic or pyramidal surface region including one or more generally flat surface regions (e.g., as shown 1032), and any combination thereof, to provide, respectively, piercing and cutting actions. In addition other modes of sharpening, such as and without limitation, chisel sharpening, will be employed in corresponding embodiments of the invention, according to the requirements of a particular application.

Figure 10B:
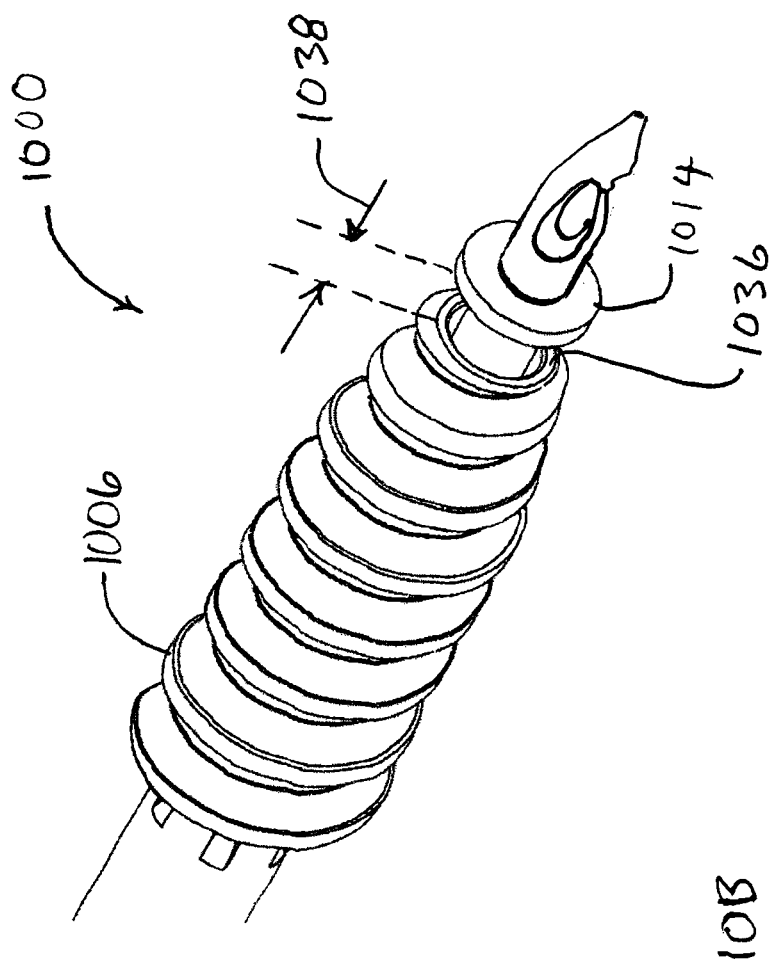
FIG. 10B shows, in schematic perspective view, a further surgical tool prepared according to principles of the invention in a retracted view.

In light of the foregoing disclosure, the reader will appreciate that the surgical tool 1000 is shown in an extended configuration such that distance 1034 between washer 1014 and a distal end 1036 of bone anchor 1006 is relatively long, as compared to the corresponding dimension of the same surgical tool when disposed in a retracted configuration. Such a retracted configuration is illustrated in FIG. 10B. As drawn, where the surgical tool 1000 is in its retracted configuration, washer 1014 is disposed relatively proximate to distal end 1036 of bone anchor 1006 and distance 1038 is consequently relatively short.

Figure 11B:
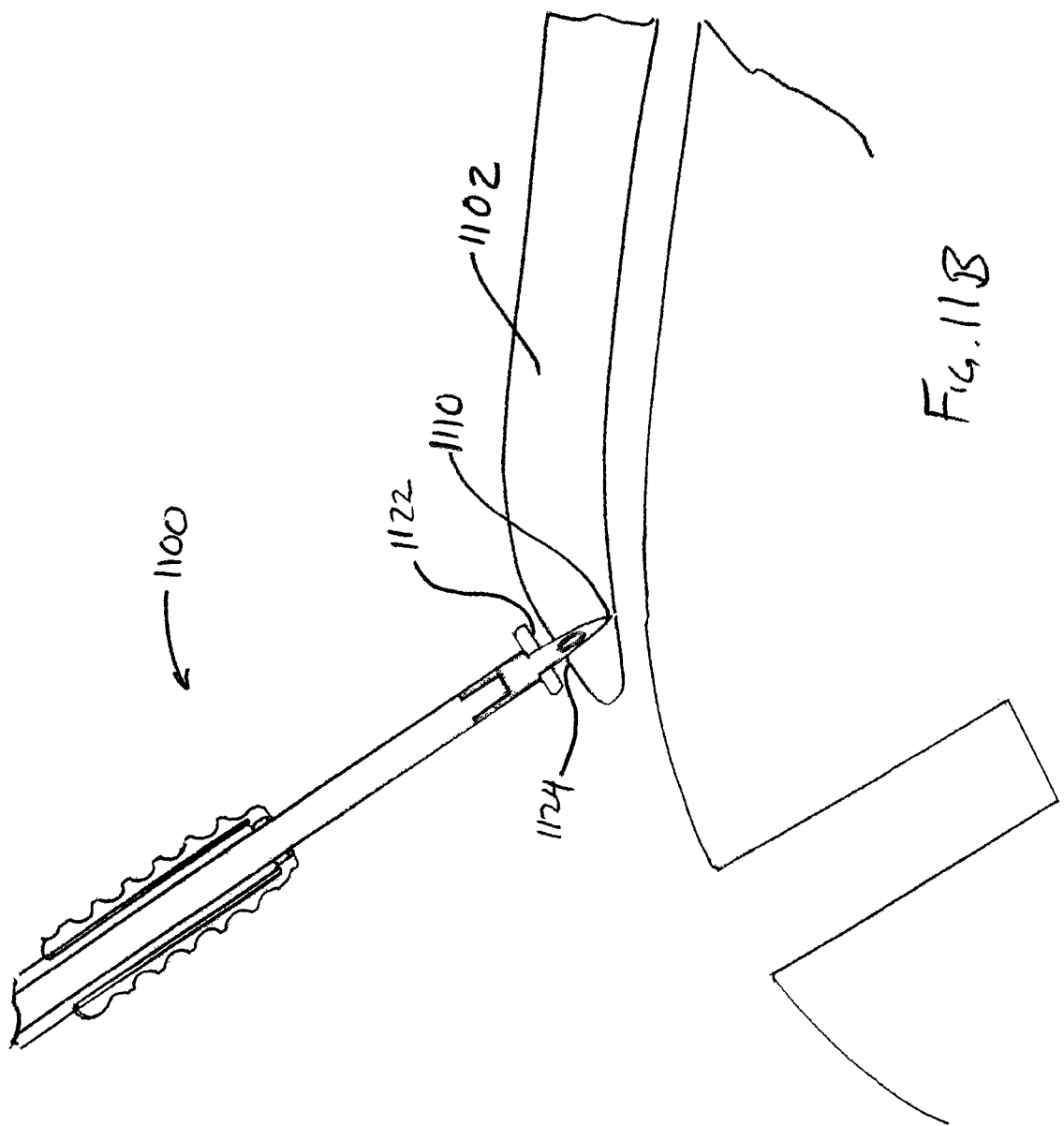
FIG. 11B shows, in schematic cross-sectional view, an exemplary state in an exemplary method of using a surgical tool.

FIGS. 11A-11H show, in schematic cross-sectional view, various states in an exemplary method of using a surgical tool 1100 similar to tool 1000 of FIGS. 10A and 10B. FIG. 11A shows surgical tool 1100, a portion of a detached tendon 1102 and a portion of a bony substrate 1104 where the tendon is to be reattached. As illustrated, a bore 1106 has been prepared in the bony substrate to receive a portion of the tendon and a bone anchor 1108.

It will be noted that a distal end 1110 of the surgical tool is pointed for piercing, and that a circumferential external surface 1112 of a shaft 1114 of the surgical tool 1100 (or of a separate tip on the shaft 1114) supports a corresponding internal surface 1116 of a bearing washer 1118. It will also be noted that the bearing washer 1118 is prevented from moving proximally along shaft 1114 by a shoulder feature 1120, and that the surgical tool 1100 is disposed in an extended configuration (as discussed in relation to FIGS. 10A-10B).

FIG. 11B shows that the surgical tool 1100 has been advanced so that distal end 1110 has pierced the tendon 1102. According to an exemplary method, tool 1100 is urged forward longitudinally until a distal surface region 1122 of bearing washer 1118 contacts a corresponding surface region 1124 of tendon 1102.

FIG. 11C shows that surgical tool 1100 has been rotated 1126 about an axis transverse to longitudinal axis 1128 of shaft 1114, and advanced 1130 towards the prepared bore 1106. Tendon 1102 is consequently moved with respect to bony substrate 1104 and stretched towards a desired attachment location.

Figure 11D:
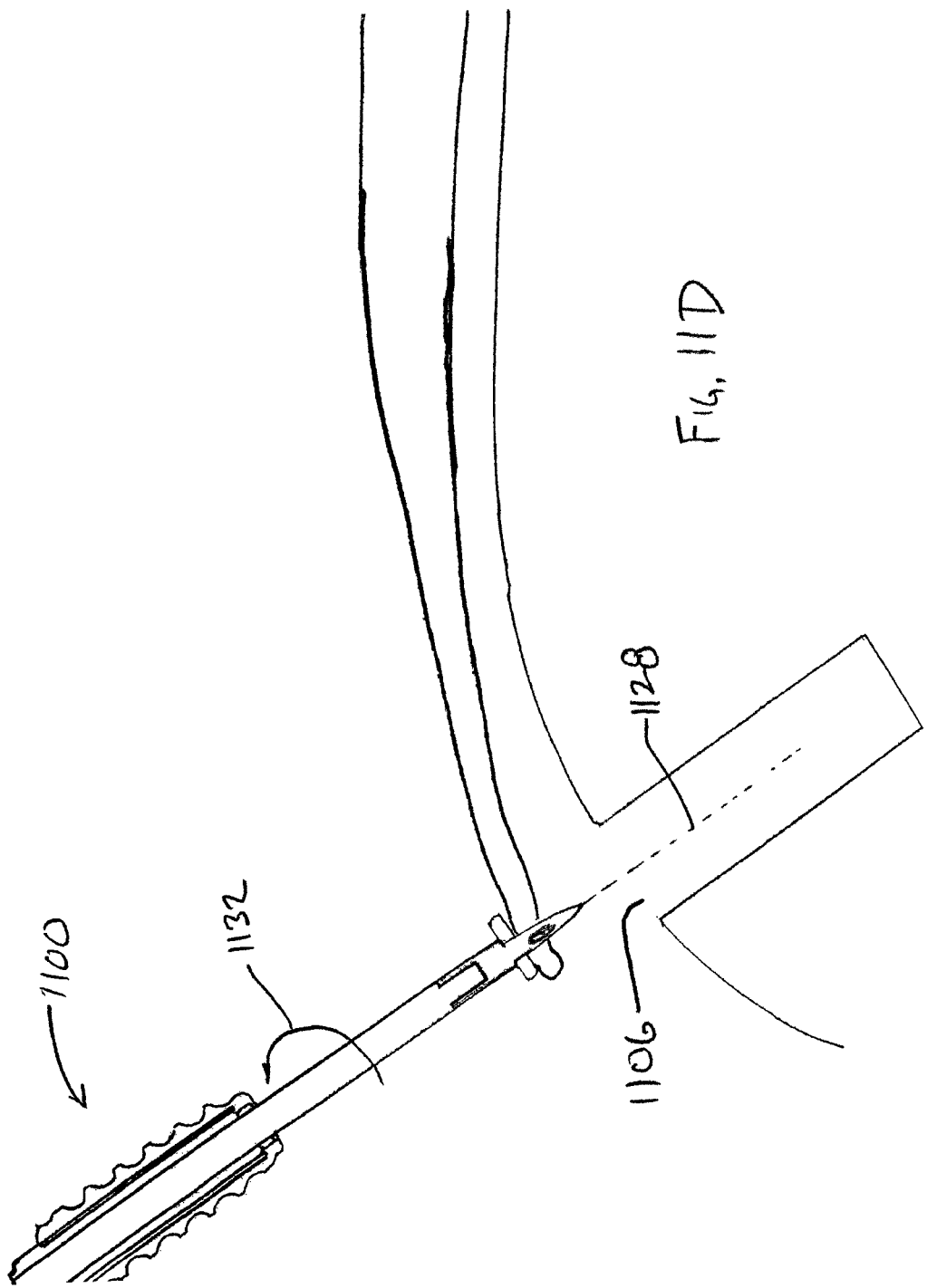
FIG. 11D shows, in schematic cross-sectional view, an exemplary state in an exemplary method of using a surgical tool.

Thereafter, as shown in FIG. 11D surgical tool 1100 is counter-rotated 1132 to bring longitudinal axis 1128 generally into alignment with a longitudinal axis of bore 1106.

Thereafter, surgical tool 1100 is advanced with a generally linear motion in direction 1134 along longitudinal axis 1128 to draw a portion 1136 of tendon 1102 into and towards the bottom surface 1140 of bore 1106, as shown in FIG. 11E. Once the tendon portion 1136 has been advanced to a desired location within bore 1106, a detent of the surgical tool is released. This allows relative longitudinal displacement of the bone anchor 1108 in direction 1134 with respect to the substrate bone 1104 and the washer 1118.

FIG. 11F shows a state of the surgical tool, in which a distal end 1141 of the bone anchor 1108 has been advanced into contact with a proximal edge 1142 of bore 1106 (i.e., the mouth of the bore), and into contact with a surface region 1144 the tendon 1102. This brings helical threads e.g., 1146, of the bone anchor 1108 into an arrangement where rotation of the bone anchor 1108 about longitudinal axis 1128 causes the threads of the bone anchor to further engage with the surrounding bone and soft tissue so as to advance the bone anchor towards the bottom 1140 of the bore 1106.

Figure 11G:
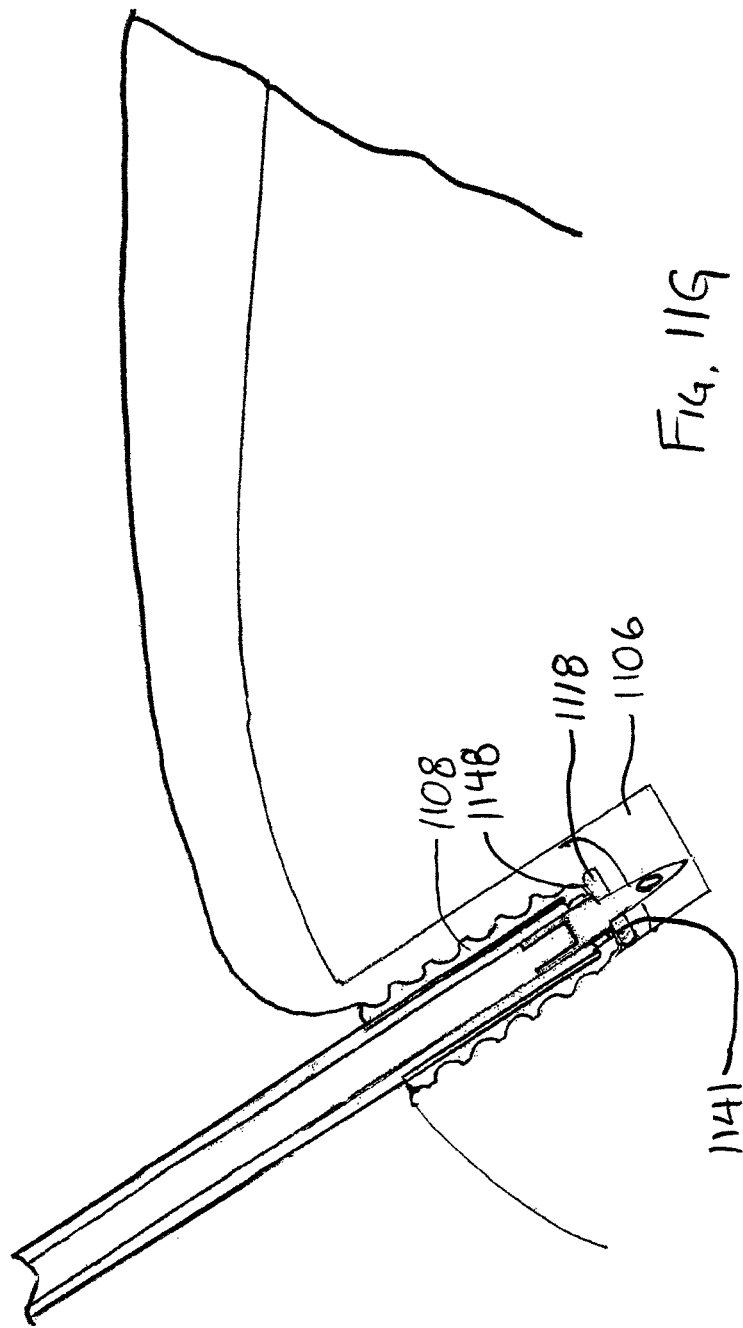
FIG. 11G shows, in schematic cross-sectional view, an exemplary state in an exemplary method of using a surgical tool.

FIG. 11G shows a condition of the assembly once the bone anchor 1108 has been rotated until fully driven into the bore 1106, such that the distal end 1141 of the bone anchor 1108 is disposed in contact with a proximal surface region 1148 of bearing washer 1118. Thereafter, as shown in FIG. 11H, the surgical tool may be withdrawn in direction 1150 along longitudinal axis 1128.

This causes the respective spline features 1152, 1154 of the surgical tool 1100 to disengage. The surgical tool is removed and the bone anchor 1108 and tendon 1102, 1136 are fixed in place. One of skill in the art will appreciate that this arrangement will hold a surface region 1156 of the tendon in direct contact with a corresponding surface region 1158 of the substrate bone, allowing regrowth and reattachment of the soft tissue and bone.

Referring again FIGS. 10A and 10B one sees an apparatus with an eyelet that, in addition to accommodating the washer above, includes an inner shaft with a slot or eyelet that allows the user to pass a suture or sutures through the soft tissue and then pass the free ends of the suture through the eyelet. Once this step is completed, the user has the soft tissue firmly attached to the device. This step adds improved ability to control and manipulate the soft tissue.

While ligament and bone have been identified in the foregoing discussion for illustrative purposes, one of skill in the art will appreciate that any variety of soft tissues and hard tissues will be joined according to the identified methods and using the identified apparatus in various combinations.

In an alternative arrangement, a surgical tool such as surgical tool 1100 is configured to be employed by passing a suture through soft tissue 1102, and wrapping the suture around a circumferential external surface 1112 of shaft 1114. The suture is then urged into bore 1106 and fixed in place by the application of the anchor 1108.

FIG. 11I shows the installation of such a suture prior to wrapping around the circumferential external surface 1112. Moreover, and as discussed above, in certain embodiments an eyelet (as shown 1031 in FIG. 10 above) is provided as part of a suture loop feature of the shaft 1114. Thus, FIG. 11I shows a needle 1170 (or, e.g. a suture passer) passing a portion of a suture 1172 through an exemplary detached tendon 1102.

Figure 11J:
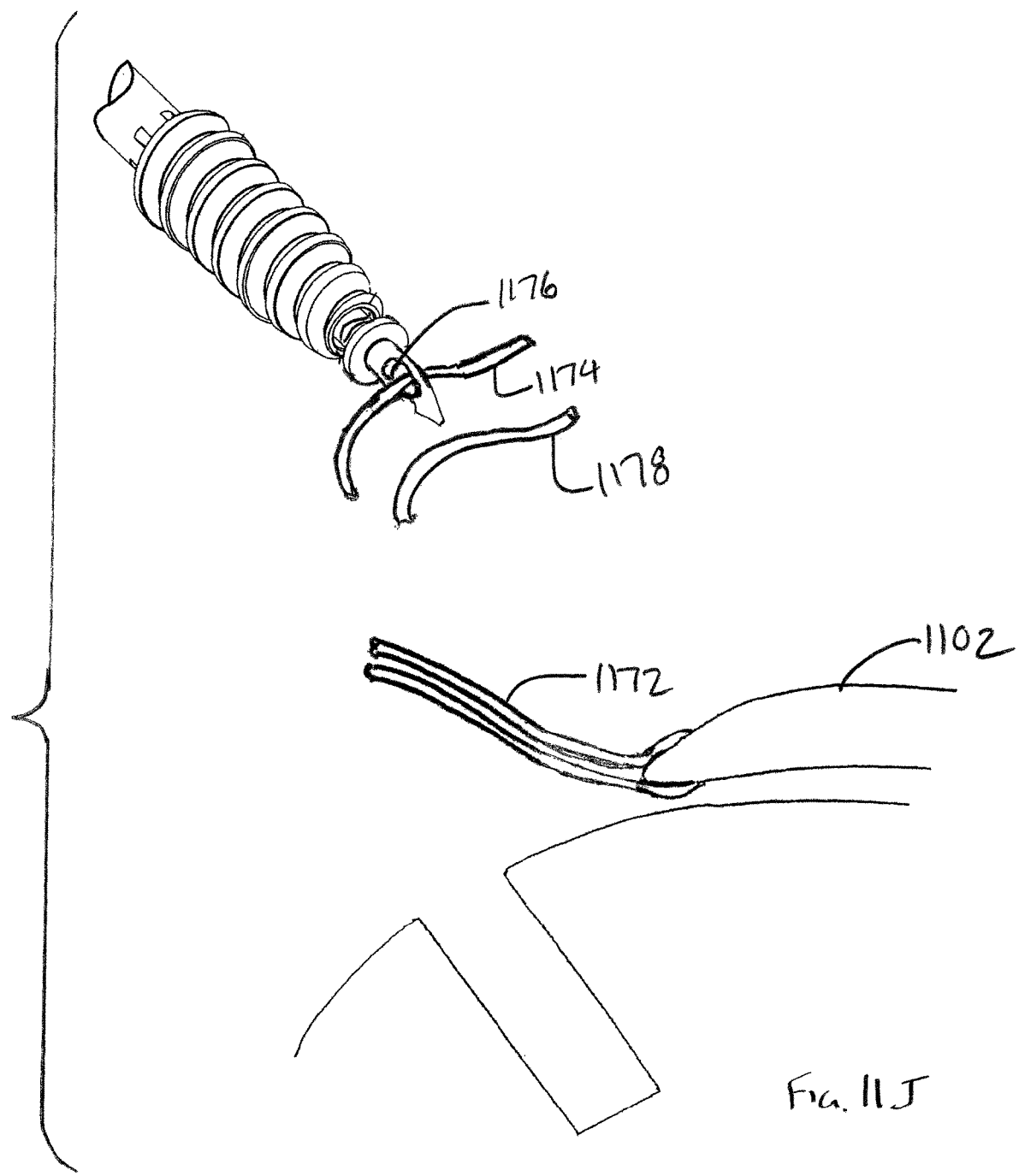
FIG. 11J shows, in schematic cross-sectional view, an exemplary state in an exemplary method of using a surgical tool.

FIG. 11J shows the suture 1172 passed through the tendon 1102 and withdrawn from the surgical site. Thereafter, one portion 1174 of the suture is installed within an eyelet 1176 and gentle tension is applied as the suture guides the suture loop down to the end of the tendon 1102. As described above, the pointed end of the suture loop is pressed into the tendon in anticipation of an interference fit fixation.

Figure 11K:
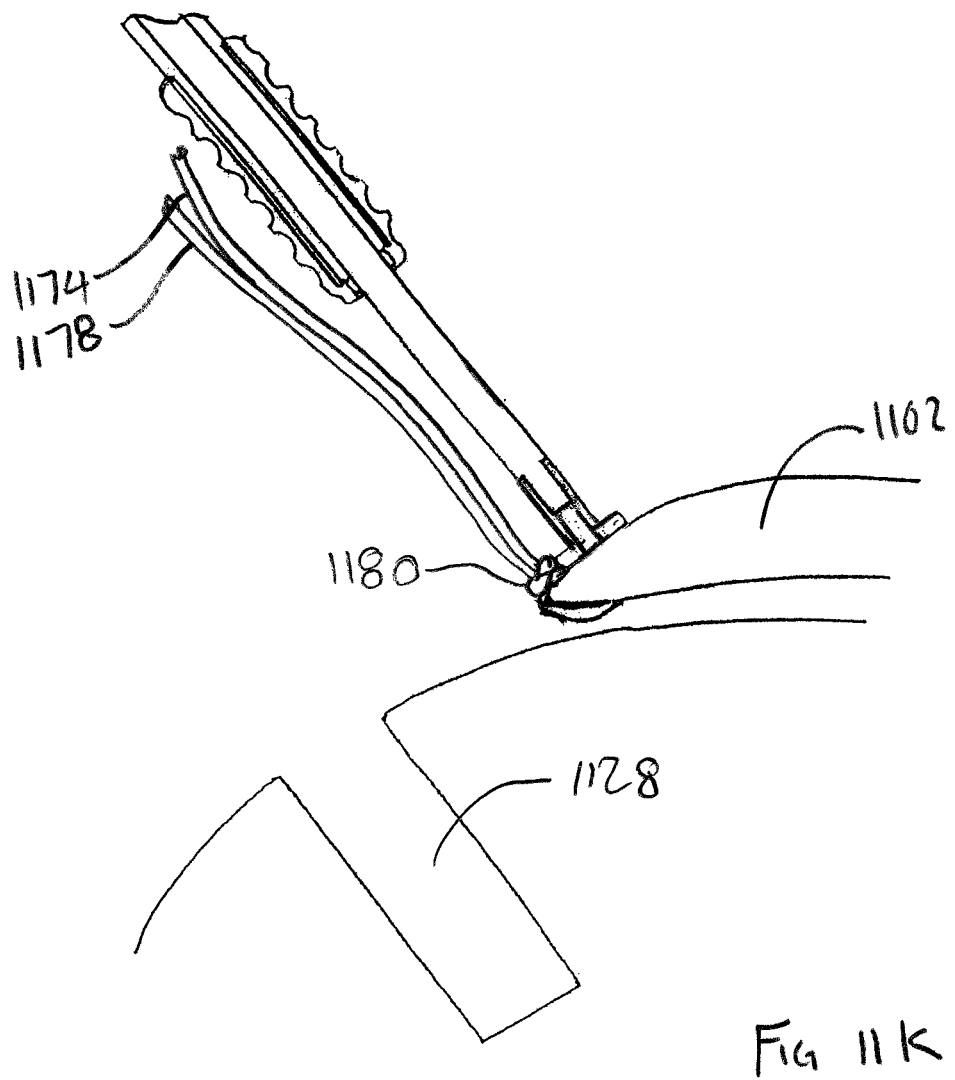
FIG. 11K shows, in schematic cross-sectional view, an exemplary state in an exemplary method of using a surgical tool.

Thereafter an arthroscopic sliding knot 1180 is tied in the external ends 1174, 1178 of the suture and drawn down to the interface between the tendon 1102 and suture loop apparatus as shown in FIG. 11K. This tends to help secure the tendon 1102 to the end of the surgical apparatus, and further makes suture ends 1174, 1178 available to assist in positioning of the soft tissue with respect to the prepared bore 1128.

Figure 11L:
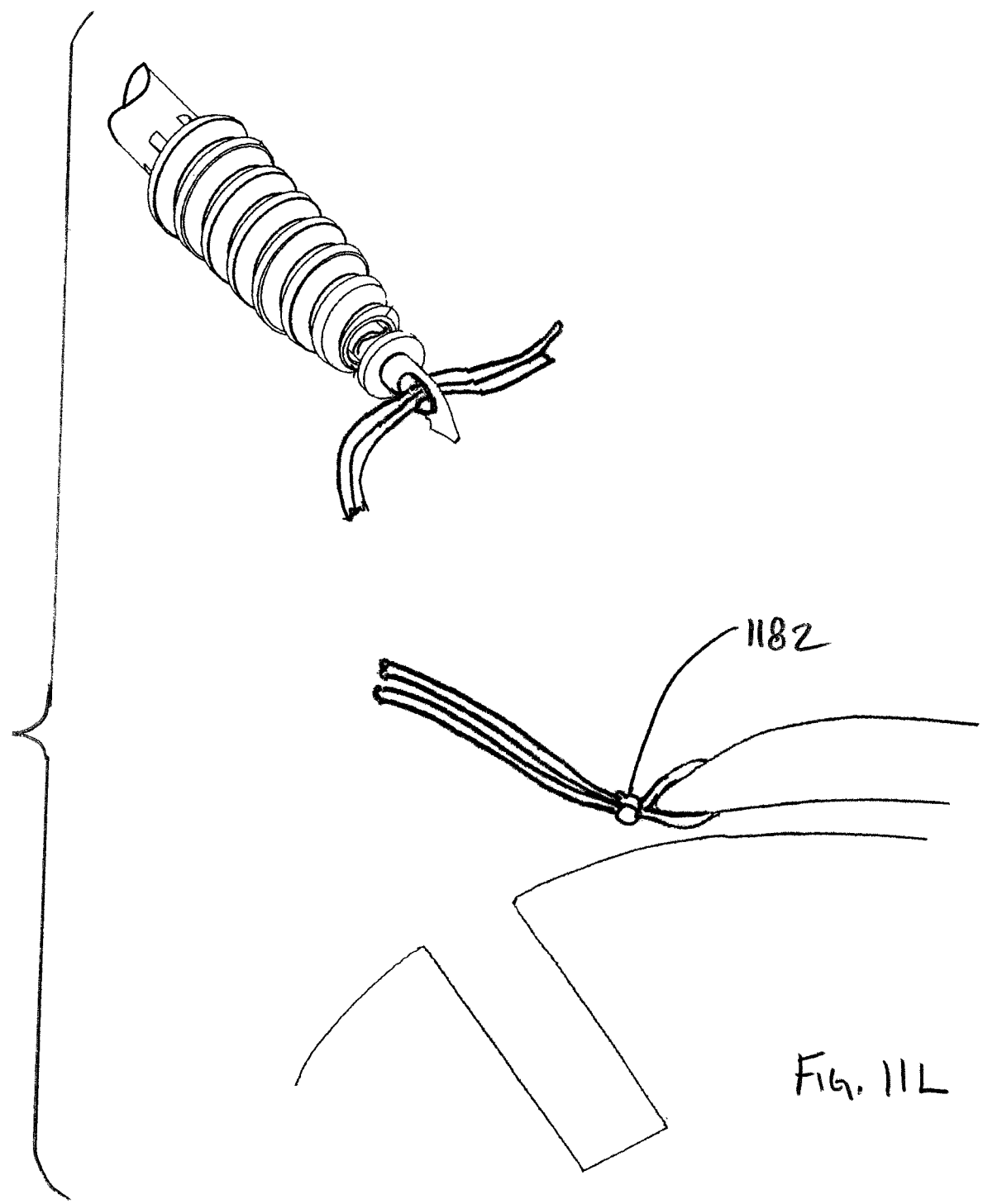
FIG. 11L shows, in schematic cross-sectional view, an exemplary state in an exemplary method of using a surgical tool.

FIG. 11L shows an alternative arrangement in which the surgical knot 1182 is tied prior to insertion of the suture loop into the tendon 1102.

Figure 12:
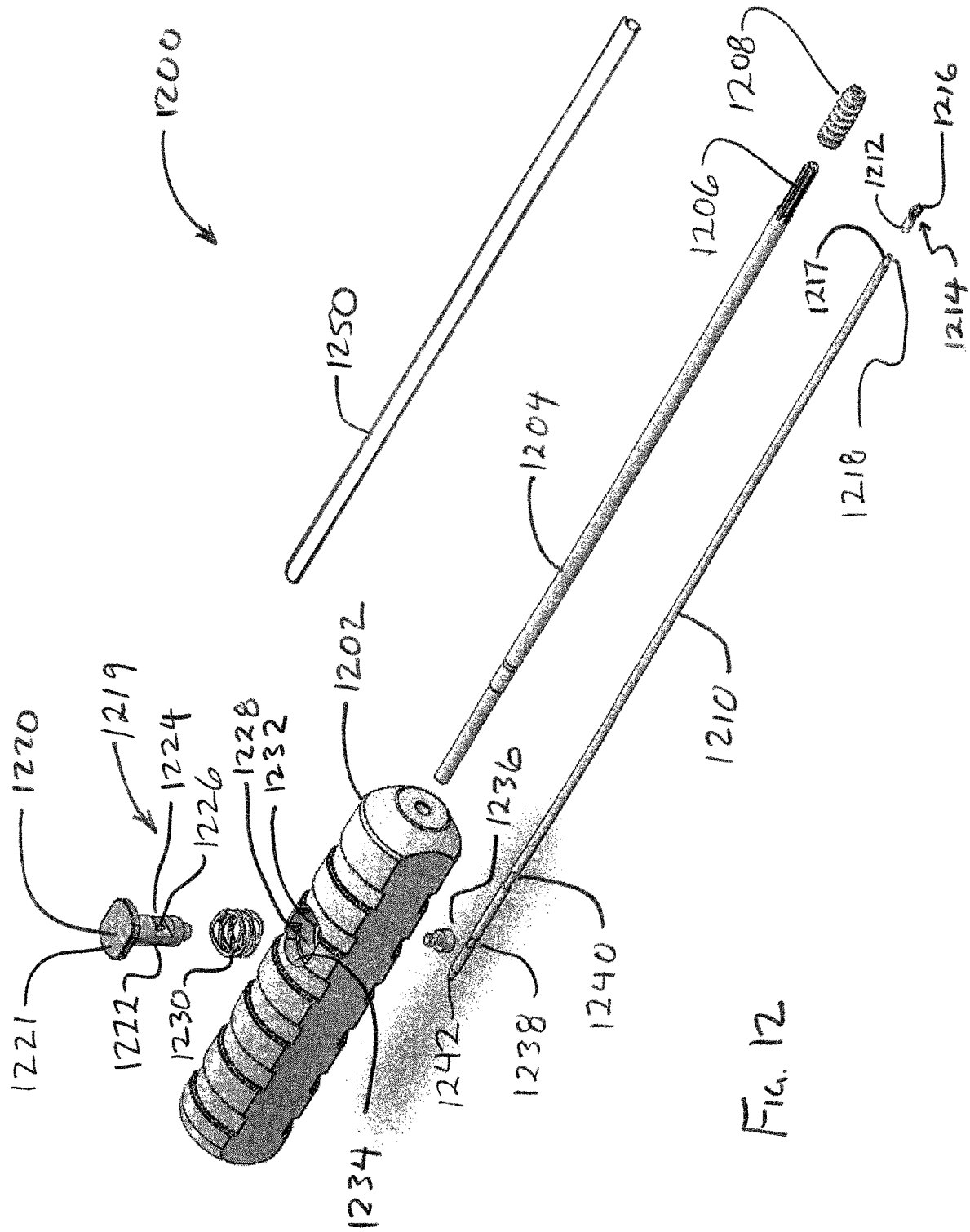
FIG. 12 shows, in exploded view, an exemplary surgical tool according to principles of the invention.

FIG. 12 shows, in exploded perspective view, an exemplary surgical tool 1200 prepared according to principles of the invention. The surgical tool 1200 includes a handle member 1202. The handle member 1202 is substantially fixedly coupled to a cannular anchor driver 1204 such that a longitudinal axis of the handle member and a longitudinal axis of the cannular anchor driver are substantially coincident.

The cannular anchor driver 1204 includes, on an external circumferential surface of its distal end, a spline feature 1206. The spline feature 1206 is sized and arrange to couple with, and be complementary to, an internal spline feature of a bone anchor 1208. The bone anchor 1208 is shown as having an external helical thread for engaging with an internal circumferential surface of a bore in a substrate. One of skill in the art will appreciate that any of the bone anchors presented in this application need not be helically threaded, but may include any of a wide variety of bone anchors including, for example and without limitation, a barbed bone anchor, an adhesively mounted bone anchor, and any combination thereof.

Disposed within a longitudinal cannula (or bore) of the cannular anchored driver 1204 is a suture guide shaft 1210. The suture guide shaft is substantially fixedly coupled, at a distal end thereof, to a suture guide 1212. The suture guide includes, at its distal end, a generally toroidal feature 1214 such as, for example, an eyelet. The toroidal feature defines an aperture 1216 with an internal bearing surface region for encircling and controlling a portion of a suture or other material.

The longitudinal axis of the suture guide shaft 1210 lies generally within a plane of the aperture 1216. A longitudinal axis of the aperture through the plane of the aperture is disposed generally transverse to the longitudinal axis of the suture guide shaft 1210. When the suture guide shaft 1210 is in use, it is disposed within the cannula of the cannular anchor driver 1204, such that the cannular anchor driver at the suture guide shaft are arranged generally coaxial to one another.

In the illustrated embodiment, the suture guide shaft 1210 includes, near its distal end, an externally threaded coupling feature 1218 and suture guide support shoulder 1217. These serve to substantially fixedly couple the suture guide shaft 1210 to the suture guide 1212. One of skill in the art will understand that, in various embodiments, the suture guide shaft 1210 and suture guide 1212 will be coupled in any effective way known, or that becomes known, in the art. Moreover, in certain embodiments, the suture guide shaft 1210 and suture guide 1212 will be integrally formed as a single component.

Also illustrated are components of a detent mechanism 1219 of the surgical tool 1200. These include a release button member 1220, having a generally planar upper surface region 1221 and a detent shaft 1222 with a generally cylindrical external surface region. A detent shaft relief feature 1224 describes a recess formed in the detent shaft 1222. The release button member 1220 also includes a suture guide shaft aperture 1226 disposed through the detent shaft 1222 within the detent shaft relief feature 1224 and generally transverse to a longitudinal axis of the release button member 1220.

The handle member 1202 includes a detent shaft aperture 1228 with the longitudinal axis generally transverse to the longitudinal axis of the surgical tool handle member 1202. The detent shaft aperture 1228 is configured to receive the detent shaft 1222 slidingly therewithin. A detent spring 1230 is sized and configured to be disposed within a recess 1232 arranged within the handle member 1202 coaxially around detent shaft aperture 1228. As will be evident to the reader, the detent shaft 1222 is sized and configured to be disposed within an internal region defined by the detent spring 1230.

The illustrated detent spring 1230 is shown as a plurality of Belleville washers. One of skill in the art will appreciate, that other configurations, including any spiral spring, elastomeric tube, or other elastic member will be used in corresponding embodiments of the invention according to the requirements of a particular application.

The recess 1232 is defined by an internal surface region of a suture guide release button relief 1234, such that the release button member 1220 can move radially into the handle by compression of spring 1230 when an inward radial force is applied to upper surface region 1221.

A detent shaft retainer fastener 1236 is configured to be coupled to a lower end of the release button member 1220 (e.g., by a threaded coupling, a weldment, a chemical adhesive, etc.) so as to retain the release button member 1220 and detent spring 1230 in place.

As illustrated, the suture guide shaft 1210 includes first 1238 and second 1240 capture relief features near a proximal end of the suture guide shaft. The suture guide shaft 1210 also includes a tapered feature 1242 immediately adjacent its proximal end. As will be further discussed and illustrated below, first 1238 and second 1240 capture relief features are arranged and configured to be releasably captured at the detent shaft relief feature 1224 when the suture guide shaft 1210 is disposed within the suture guide shaft aperture 1226 of the detent shaft 1222.

As illustrated, in certain embodiments a further sheath 1250 is disposed coaxially around the outside of cannular anchor driver 1204.

Figure 13:
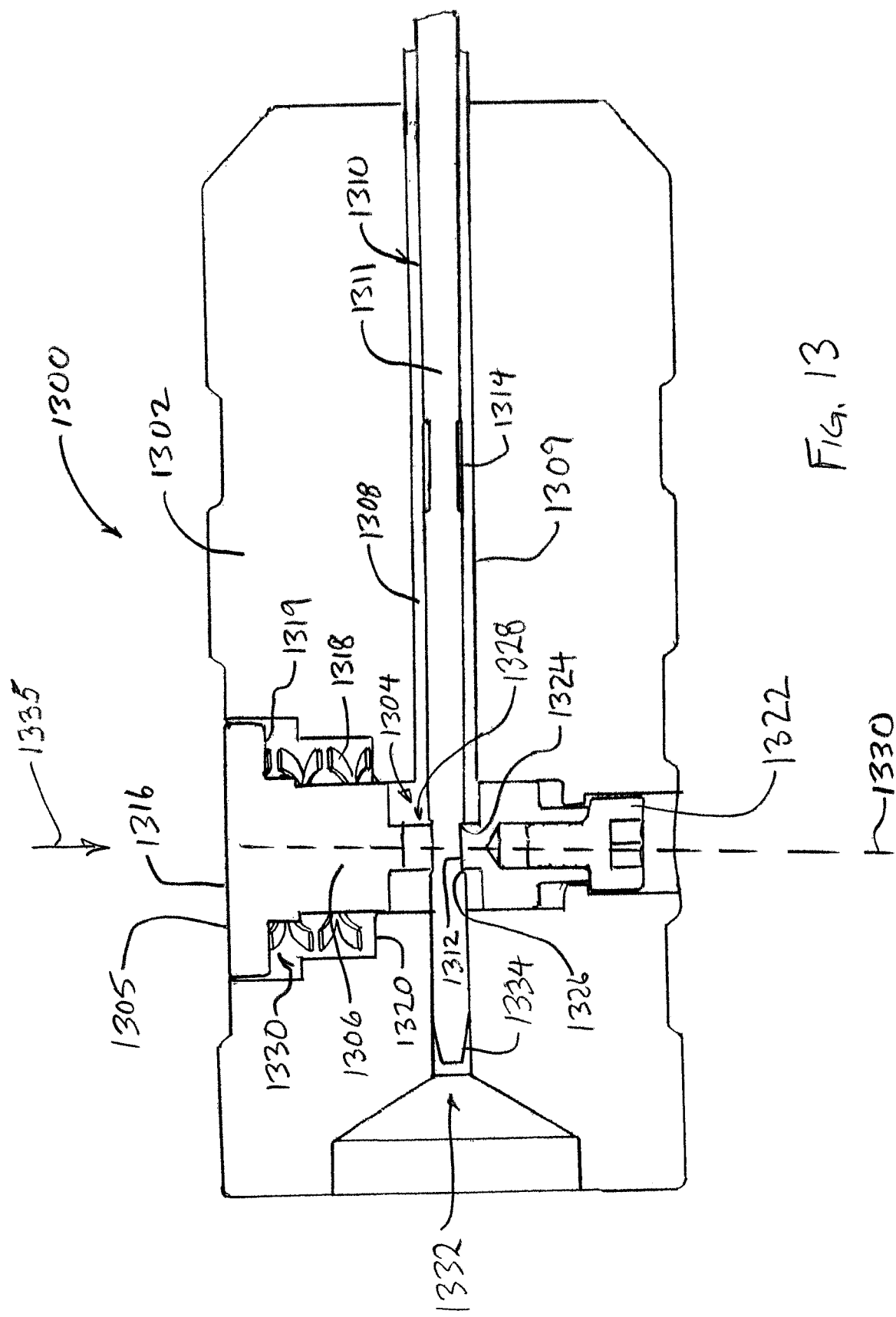
FIG. 13 shows, in schematic cross-section, a handle portion of a surgical tool prepared according to principles of the invention.

FIG. 13 shows, in cross-section, a portion of an exemplary surgical tool 1300 prepared according to principles of the invention. Surgical tool 1300 includes a handle member 1302 with a detent shaft aperture 1304. A detent member 1305 including a detent shaft 1306 is disposed coaxially within the detent shaft aperture 1304. Transverse to the detent shaft aperture 1304, a cannular anchor driver 1308 is substantially fixedly disposed coaxially within a further bore 1309 of the handle member 1302.

Slidingly disposed within a cannula 1310 of the cannular anchor driver 1308 is a suture guide shaft 1311. The guide shaft is relieved at two locations along its length; an extended guide shaft relief 1312, and a retracted guide shaft relief 1314. One of skill in the art will readily understand that the guide shaft is adapted to be arrested in its longitudinal motion by a detent mechanism of the handle at either of the extended guide shaft relief 1312 and the retracted guide shaft relief 1314.

The suture guide shaft 1311, is rotatable within the cannula 1310 when captured by the detent mechanism at both of the extended configuration and the retracted configuration. That is, the handle member 1302 can be co-rotated with the cannular anchor driver 1308 about a longitudinal axis common to the handle, the cannular anchor driver 1308 and the suture guide shaft 1311 while the suture guide shaft 1311 remains static and does not rotate.

In order to allow this relative rotation of the handle member 1302 and cannular anchor driver 1308 with respect to the suture guide shaft 1311, the cross-sections of the suture guide shaft 1311 and both the extended 1312 and retracted 1314 reliefs of the suture guide shaft are substantially circular.

In other embodiments, the detent mechanism is arranged to prevent rotation of the suture guide with respect to the cannular anchor driver until the detent mechanism is released.

The detent member 1305 includes a suture guide release button 1316. One end of a detent spring 1318 is located proximal to a lower surface 1319 of the suture guide release button 1316. An opposite end of the detent spring 1318 is supported by a detent spring shoulder 1320. The detent spring 1318 is arranged to urge the lower surface 1319 of the suture guide release button 1316 away from the detent spring shoulder 1320. This motion is limited by a detent shaft retainer fastener 1322 in a manner that will be evident to one of skill in the art.

Detent shaft 1306 includes a detent shaft aperture 1328 which is located substantially perpendicular to a longitudinal axis 1330 of the detent shaft 1306. By urging the lower surface 1319 of the suture guide release button 1316 away from the detent spring shoulder 1320, the detent spring 1318 tends to maintain circumferential edges 1324, 1326 of the detent shaft aperture 1328 in contact with corresponding edge regions of the guide shaft reliefs 1312, 1314 so as to temporarily substantially fix the longitudinal position of the suture guide shaft 1311 with respect to the handle 1302 and cannular anchor driver 1308.

It will be noted that a proximal end 1332 of the suture guide shaft 1311 includes a generally conically tapered region 1334. This conically tapered region 1334 facilitates initial insertion of the suture guide shaft 1311 into the apparatus and past edge 1324 of the detent shaft aperture 1328.

Upon inspection, it will be clear to one of skill in the art that, when the surgical tool 1300 is in use, urging the suture guide release button 1316 inwardly 1335 will tend to release the engagement of circumferential edges 1324 and 1326 from the extended guide shaft relief 1312 so that the suture guide shaft 1311 can slide longitudinally and distally within cannula 1310. If the suture guide release button 1316 is thereafter released, when suture guide release 1314 arrives at the detent shaft aperture 1328, the action of detent spring 1318 will urge the detent shaft into engagement with retracted relief 1314. This corresponds to the action of the surgical tool, as described above.

Figure 14:
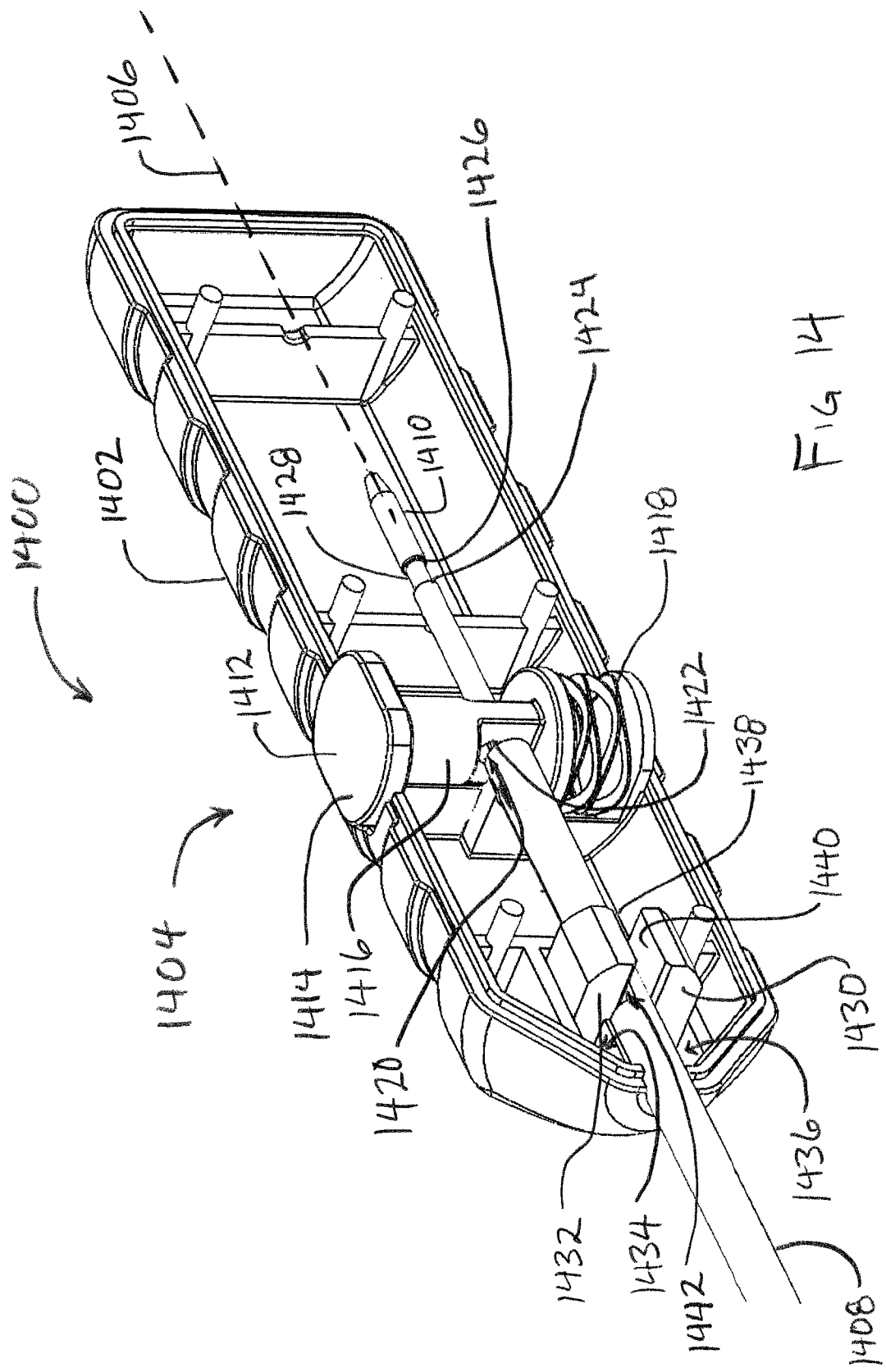
FIG. 14 shows, in schematic cross-section, a surgical tool prepared according to principles of the invention.

FIG. 14 shows, in schematic perspective view, another aspect of a surgical tool 1400 prepared according to principles of the invention. The surgical tool 1400 includes a handle member 1402. Disposed within the handle member 1402 is a detent mechanism 1404. A longitudinal axis 1406 is common to the handle member 1402, a cannular anchor driver 1408 and a suture guide shaft 1410 disposed within a cannula of the cannular anchor driver 1408.

The detent mechanism 1404 includes a detent member 1412 with a suture guide release button 1414 a detent shaft 1416 detent spring 1418 and a suture guide aperture 1420. In the manner discussed above, the suture guide aperture 1420 embodies edges 1422 that interfere with and temporarily capture corresponding edges e.g., 1424, 1426 of an extended suture guide relief 1428, and a retracted suture guide relief (not visible).

It will be noted that, in contrast to surgical tool 1300 of FIG. 13, detent spring 1418 of surgical tool 1400 is disposed relatively distal to release button 1414 of detent member 1412, as compared to detent spring 1318 and release button 1316.

Handle member 1402 also includes first 1430 and second 1432 distal jaw members. Distal jaw members 1430 and 1432 are disposed within respective recesses 1434, 1436 of handle member 1402. The jaw members 1430 and 1432 have respective contact surface regions 1438, 1440. In the illustrated embodiment, cannular anchor driver 1408 includes jaw apertures, e.g. 1442.

In certain embodiments of the invention, distal jaw members 1430 and 1432 tend to impinge within the jaw apertures, e.g. 1442, to retain cannular anchor driver 1408 longitudinally and rotationally in place within the handle member 1402. In such embodiments, cannular anchor driver 1408 may be removably installed within handle member 1402 and securely retained therein during operation of the surgical tool 1400.

In certain embodiments, the contact surface regions 1438 and 1440 are arranged to impinge on an external circumferential surface region of suture guide shaft 1410, thereby providing a desirable resistance to rotation of the suture guide shaft 1410 with respect to handle member 1402 while still allowing the suture guide shaft to rotate.

In various embodiments of the invention, the distal jaw members 1430 and 1432 include one or more of an elastomeric polymer material, a thermoplastic polymer material, a thermoset polymer material, and a metallic material. In other embodiments, other materials will be employed to achieve desirable characteristics to achieve the functions described above.

A method according to principles of the invention includes:

1. Place sutures through the targeted tissue as required.
2. Create a hole to accommodate the selected diameter anchor to the proper depth using a purpose designed drill bit and guide. The guide may or may not be required.
3. Aseptically open the driver and anchor and place the anchor onto the driver.
4. Thread previously placed sutures placed through the Suture Guide located on the distal end of the driver.
5. Insert the Suture Guide with handle into the hole created in step 2.
6. Remove any slack in the suture and create the desired amount of tension by pulling on the suture tails.
7. Push the handle with the anchor firmly into the hole, until the anchor contacts the suture. This action will maintain the desired tension on the suture.
8. Depress the button on the handle and begin to insert the anchor into the hole by turning the handle in a clockwise direction.
9. Continue insertion until an audible "click" is heard. This will signal the proper depth of the implant, which should be slightly below the surface of the surrounding bone.
10. Remove the handle from the implant by pulling it along the axis of insertion.
11. Trim the access suture tails as desired.

While the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. A method of preparing an implant insertion system comprising:
   providing a shaft, said shaft having a proximal end, a distal end, and a longitudinal axis;
   disposing a spine portion of a suture loop feature proximate to said distal end of said shaft, said spine portion of said suture loop feature having a first proximal end, a second distal end and a first surface region;
   disposing a latch portion of said suture loop feature proximate to said distal end of said shaft, said latch portion of said suture loop feature having a third proximal end, a fourth distal end and a second surface region, said third proximal end being connected to said spine portion of said suture loop feature at said first proximal end of said spine portion; and
   disposing said fourth distal end of said latch portion in contact with said spine portion such that said first surface region is disposed in spaced relation to said second surface region across said longitudinal axis, and such that said contact between said fourth distal end of said latch portion and said spine portion tends to retain a suture between said first surface region and said second surface region.

2. The method of preparing the implant insertion system as defined in claim 1 wherein said disposing said spine portion of said suture loop feature proximate to said distal end of said shaft comprises integrally forming said spine portion of said suture loop feature adjacent to said distal end of said shaft.

3. The method of preparing the implant insertion system as defined in claim 1 wherein said third proximal end of said latch portion being connected to said spine portion of said suture loop feature at said first proximal end of said spine portion comprises said third proximal end being integrally formed with said spine portion of said suture loop feature at said first proximal end of said spine portion.

4. The method of preparing the implant insertion system as defined in claim 1 wherein said third proximal end of said latch portion being connected to said spine portion of said suture loop feature at said first proximal end of said spine portion comprises forming said latch portion as a discrete component and thereafter coupling said latch portion to said spine portion of said suture loop feature.

5. The method of preparing the implant insertion system as defined in claim 1 wherein said disposing said fourth distal end of said latch portion in contact with said spine portion comprises bending said latch portion towards said longitudinal axis.

6. The method of preparing the implant insertion system as defined in claim 1 wherein said disposing said fourth distal end of said latch portion in contact with said spine portion comprises bending said latch portion into a substantially concave curve with respect to said longitudinal axis.

7. The method of preparing the implant insertion system as defined in claim 1 further comprising disposing a washer element coaxially about said shaft distally of said spine portion.

8. The method of preparing the implant insertion system as defined in claim 7 further comprising supporting said washer element against distal motion along said longitudinal axis by disposing a distal surface region of said washer element against a corresponding surface region of said shaft.

9. The method of preparing the implant insertion system as defined in claim 8 wherein said corresponding surface region of said shaft comprises a substantially radial surface region of said shaft.

10. The method of preparing the implant insertion system as defined in claim 9 wherein said washer element is adapted to be released from said shaft during coupling of said suture to a substrate.

* * * * *